US009994644B2

(12) United States Patent
Wong et al.

(10) Patent No.: US 9,994,644 B2
(45) Date of Patent: Jun. 12, 2018

(54) MAB 2 ANTI-MET ANTIBODY

(71) Applicant: Agency for Science, Technology and Research, Singapore (SG)

(72) Inventors: Shuxian Julin Wong, Singapore (SG); David Philip Lane, Singapore (SG)

(73) Assignee: Agency for Science, Technology and Research, Singapore (SG)

(*) Notice: Subject to any disclaimer, the term of this patent is extended or adjusted under 35 U.S.C. 154(b) by 0 days. days.

(21) Appl. No.: 14/888,354

(22) PCT Filed: Mar. 28, 2014

(86) PCT No.: PCT/SG2014/000144
§ 371 (c)(1),
(2) Date: Oct. 30, 2015

(87) PCT Pub. No.: WO2014/178791
PCT Pub. Date: Nov. 6, 2014

(65) Prior Publication Data
US 2016/0083479 A1 Mar. 24, 2016

(30) Foreign Application Priority Data

Apr. 30, 2013 (SG) .............................. 201303329-5
Aug. 23, 2013 (SG) .............................. 201306428-2

(51) Int. Cl.
*C07K 16/32* (2006.01)
*C07K 16/28* (2006.01)
*G01N 33/574* (2006.01)
*A61K 47/48* (2006.01)

(52) U.S. Cl.
CPC ........ *C07K 16/32* (2013.01); *A61K 47/48384* (2013.01); *A61K 47/48569* (2013.01); *C07K 16/2863* (2013.01); *G01N 33/57492* (2013.01); *C07K 2317/34* (2013.01); *C07K 2317/622* (2013.01); *C07K 2317/73* (2013.01); *C07K 2317/76* (2013.01); *C07K 2317/77* (2013.01); *C07K 2317/94* (2013.01); *G01N 2333/71* (2013.01)

(58) Field of Classification Search
None
See application file for complete search history.

(56) References Cited

U.S. PATENT DOCUMENTS

| 8,163,280 B2 | 4/2012 | Michaud et al. |
| 2011/0239316 A1 | 9/2011 | Goetsch et al. |
| 2012/0156206 A1 | 6/2012 | Hultberg et al. |
| 2013/0089542 A1 | 4/2013 | Lee et al. |

FOREIGN PATENT DOCUMENTS

| WO | WO-2010059654 A1 | 5/2010 | |
| WO | WO 2011/150454 A1 * | 12/2011 | ............. C07K 16/28 |
| WO | WO-2011150454 A1 | 12/2011 | |
| WO | WO-2012/059561 A1 | 5/2012 | |
| WO | WO-2013051878 A2 | 4/2013 | |

OTHER PUBLICATIONS

Rudikoff et al. (PNAS USA, 1982, 79: 1979-1983).*
Coleman et al. (Research in Immunology, 1994; 145(1): 33-36).*
Abaza et al. (Journal of Protein Chemistry, vol. 11, No. 5, 1992, pp. 433-444).*
Gussow et al. (1991, Methods in Enzymology 203:99-121).*
Ibragimova and Wade (Biophysical Journal, Oct. 1999, vol. 77, pp. 2191-2198).*
Abounader, R., et al., "Signaling pathways in the induction of c-met receptor expression by its ligand scatter factor/hepatocyte growth factor in human glioblastoma", Journal of Neurochemistry, 2001, 76, 1497-1508, (2001), 1497-1508.
Adams, Gregory P., "Monoclonal antibody therapy of cancer", Nature Biotechnology, vol. 23, No. 9, Sep. 2005, 1147-1157, (Sep. 7, 2005), 1147-1157.
Bellon, Steven F., et al., "c-Met Inhibitors with Novel Binding Mode Show Activity against Several Hereditary Papillary Renal Cell Carcinoma-related Mutations", Journal of Biological Chemistry, vol. 283, No. 5, pp. 2675-2683, Feb. 1, 2008, (Nov. 30, 2007), 2675-2683.
Berthou, Sylvie, et al., "The Met kinase inhibitor SU11274 exhibits a selective inhibition pattern toward different receptor mutated variants", Oncogene (2004) 23, 5387-5393, (Apr. 5, 2004), 5387-5393.
Birchmeier, Carmen, et al., "Met, Metastasis, Motility and More", Molecular Cell Biology, vol. 4, Dec. 2003, 915-925, (Dec. 2003), 915-925.
Brockmann, Marc A., et al., "Inhibition of Intracerebral Glioblastoma Growth by Local Treatment with the Scatter Factor/Hepatocyte Growth Factor-Antagonist NK4", Clinical Cancer Research, vol. 9, 4578-4585, Oct. 1, 2003, (Oct. 1, 2003), 4578-4585.
Burgess, Teresa, et al., "Fully Human Monoclonal Antibodies to Hepatocyte Growth Factor with Therapeutic Potential against Hepatocyte Growth Factor/c-Met-Dependent Human Tumors", Cancer Res 2006; 66:3, Feb. 1, 2006; 1721-1729, (Feb. 1, 2006), 1721-1729.
Cao, Brian, et al., "Neutralizing monoclonal antibodies to hepatocyte growth factory scatter factor (HGFySF) display antitumor activity in animal models", PNAS, vol. 98, No. 13, Jun. 19, 2001, 7443-7448, (Jun. 19, 2001), 7443-7448.
Christensen, James G., et al., "A Selective Small Molecule Inhibitor of c-Met Kinase Inhibits c-Met-Dependent Phenotypes in Vitro and Exhibits Cytoreductive Antitumor Activity in Vivo", Cancer Research 63, 7345-7355, Nov. 1, 2003, (Nov. 1, 2003), 7345-7355.
De Souza, Errol B., et al., "Novel Therapeutic Modalities to Address Nondrugable Protein Interaction Targets", Neuropsychopharmacology Reviews (2009) 34, 142-158; doi:10.1038/npp.2008.115; published online Aug. 27, 2008, (Aug. 27, 2008), 142-158.

(Continued)

Primary Examiner — Peter J Reddig
(74) Attorney, Agent, or Firm — Schwegman Lundberg & Woessner, P.A.

(57) ABSTRACT

Antibodies specifically binding an epitope comprised in the α-chain of c-Met, modifications, compositions and uses thereof are disclosed herein.

11 Claims, 17 Drawing Sheets

(56) References Cited

OTHER PUBLICATIONS

Engelman, Jeffrey A., et al., "MET Amplification Leads to Gefitinib Resistance in Lung Cancer by Activating ERBB3 Signaling", Science 316, 1039 (2007); DOI: 10.1126/science.1141478; 1039-1043, (May 18, 2007), 1039-1043.

Garrett, Thomas P.J., et al., "Antibodies specifically targeting a locally misfolded region of tumor associated EGFR", PNAS, vol. 106, No. 13, Mar. 31, 2009, 5082-5087, (Mar. 31, 2009), 5082-5087.

Greenall, Sameer A., et al., "Non-Agonistic Bivalent Antibodies That Promote c-MET Degradation and Inhibit Tumor Growth and Others Specific for Tumor Related c-MET", PLoS ONE 7(4): e34658. doi:10.1371/journal.pone.0034658, (Apr. 12, 2012), 1-10.

Kong-Beltran, Monica, et al., "The Sema domain of Met is necessary for receptor dimerization and activation", Cancer Cell, vol. 6, Jul. 2004, 75-84, (Jul. 2004), 75-84.

Liska, David, et al., "HGF Rescues Colorectal Cancer Cells from EGFR Inhibition via MET Activation", Clin Cancer Res 2011;17:472-482, (Nov. 22, 2010), 472-482.

Ma, Wen W., et al., "Novel Agents on the Horizon for Cancer Therapy", CA Cancer J Clin 2009; 59:111-137; DOI: 10.3322/caac.20003, (Apr. 22, 2009), 111-137.

Martens, Tobias, et al., "A Novel One-Armed Anti-c-Met Antibody Inhibits Glioblastoma Growth In vivo", Clin Cancer Res 2006; 12(20); Oct. 15, 2006, 6144-6152, (Oct. 15, 2006), 6144-6152.

Michaud, Neil R., et al., "Biochemical and pharmacological characterization of human c-Met neutralizing monoclonal antibody CE-355621", mAbs, vol. 4, Issue 6, 710-723, (Sep. 24, 2012), 710-723.

Michieli, Paolo, et al., "Targeting the tumor and its microenvironment by a dual-function decoy Met receptor", Cancer Cell: Jul. 2004, vol. 6 (2004), (Jul. 2004), 61-73.

Pacchiana, Giovanni, et al., "Monovalency Unleashes the Full Therapeutic Potential of the DN-30 Anti-Met Antibody", The Journal of Biological Chemistry, vol. 285, No. 46, pp. 36149-36157, Nov. 12, 2010, (Nov. 12, 2010), 36149-36157.

Pozner-Moulis, Sharon, et al., "Antibody validation by quantitative analysis of protein expression using expression of Met in breast cancer as a model", Laboratory Investigation (2007) 87, 251-260. doi:10.1038/labinvest.3700515; published online Jan. 29, 2007, (Jan. 29, 2007), 251-260.

Prat, Maria, et al., "Agonistic monoclonal antibodies against the Met receptor dissect the biological responses to HGF", Journal of Cell Science 111, 237-247 (1998), (Dec. 23, 1997), 237-247.

Sattler, Martin, et al., "A Novel Small Molecule Met Inhibitor Induces Apoptosis in Cells Transformed by the Oncogenic TPR-MET Tyrosine Kinase", Cancer Research 63, 5462-5469, Sep. 1, 2003, (Sep. 1, 2003), 5462-5469.

Shattuck, David L., et al., "Met Receptor Contributes to Trastuzumab Resistance of Her2-Overexpressing Breast Cancer Cells", Cancer Res 2008;68:1471-1477, (Mar. 3, 2008), 1471-1477.

Tempest, P. R., et al., "Structure of the met protein and variation of met protein kinase activity among human tumour cell lines", Br. J. Cancer (1988), 58, 3-7, (Apr. 15, 1988), 3-7.

Van Der Horst, Edward Htun, et al., "Discovery of Fully Human Anti-MET Monoclonal Antibodies with Antitumor Activity against Colon Cancer Tumor Models In Vivo", Neoplasia, vol. 11, No. 4, Apr. 2009, 355-364, (Apr. 2009), 355-364.

Vergani, Elisabetta, et al., "Identification of MET and SRC Activation in Melanoma Cell Lines Showing Primary Resistance to PLX4032", Neoplasia, vol. 13, No. 12, Dec. 2011, pp. 1132-1142, (Dec. 2011), 1132-1142.

Wong, Julin Shuxian, "Targeting C-Met for Therapy", University of Dundee Thesis, (Jul. 2011), 260 pgs.

"European Application Serial No. 14791213.3, Supplementary European Search Report dated Nov. 28, 2016", 8 pgs.

"International Application No. PCT/SG2014/000144, International Search Report dated Jun. 23, 2014", 6 pgs.

International Application No. PCT/SG2014/000144, Written Opinion dated Jun. 23, 2014, 5 pgs.

\* cited by examiner

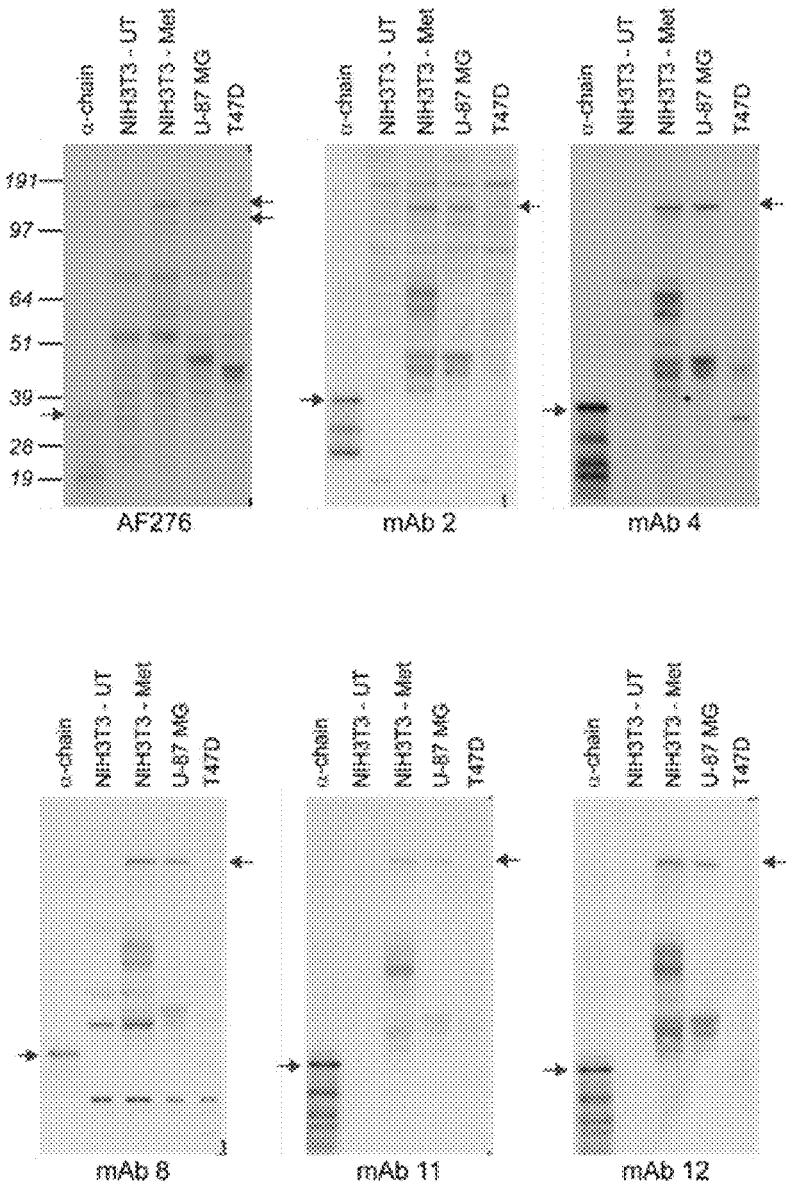

FIG. 4
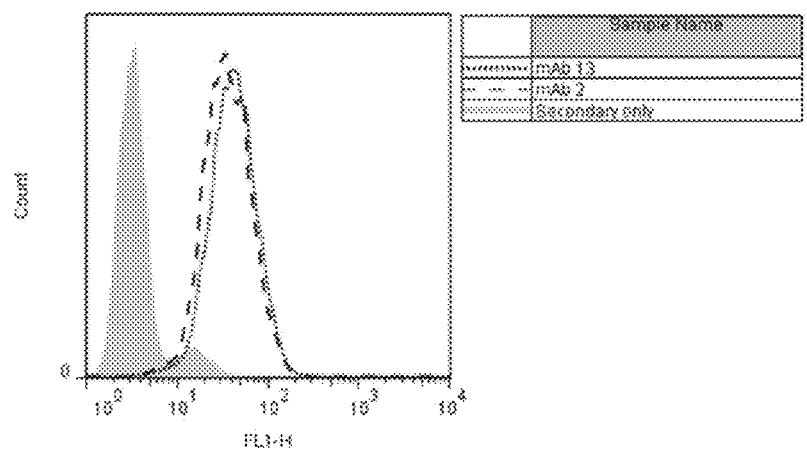
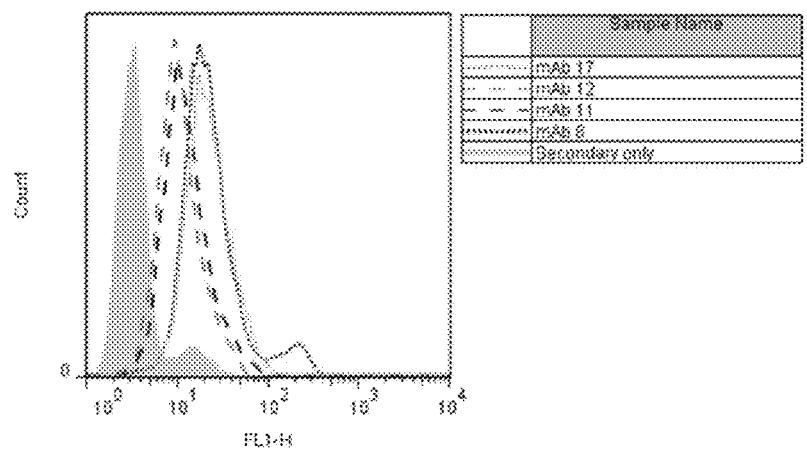
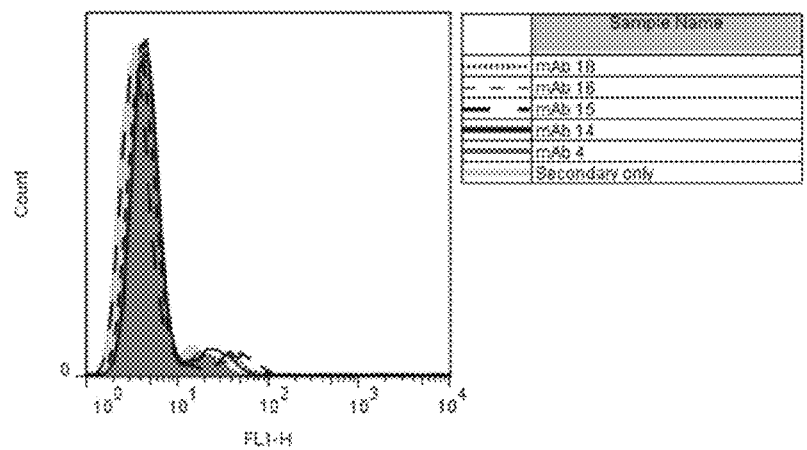

FIG. 6
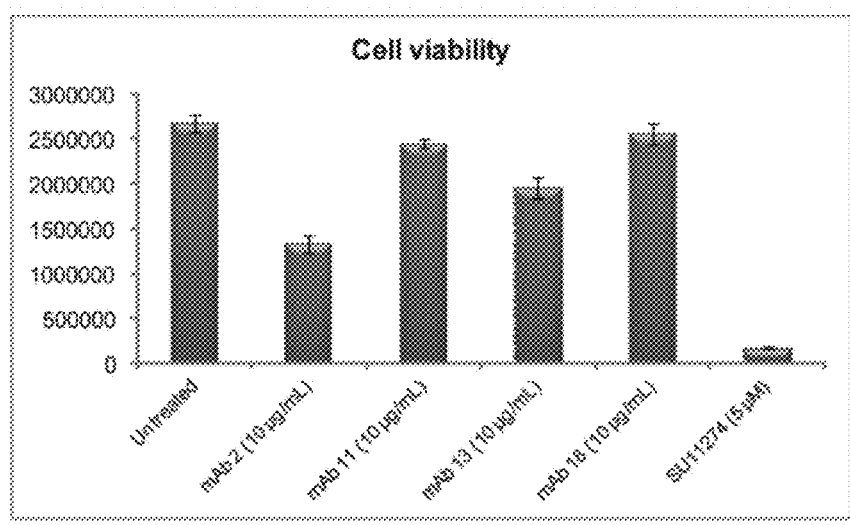
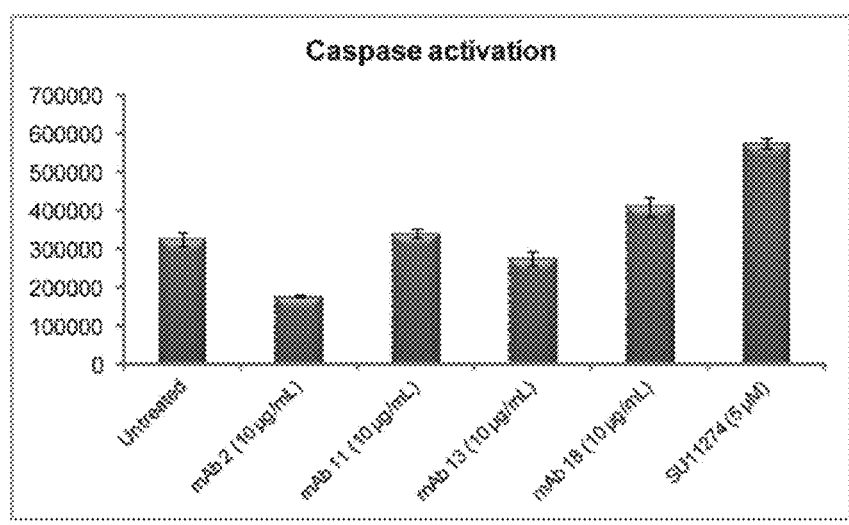

FIG. 7
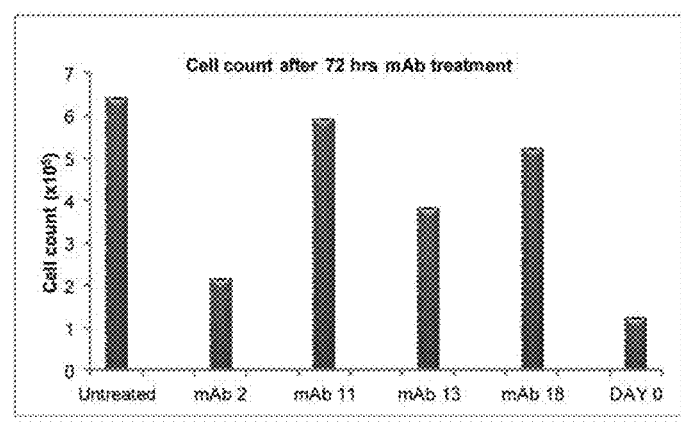
A)
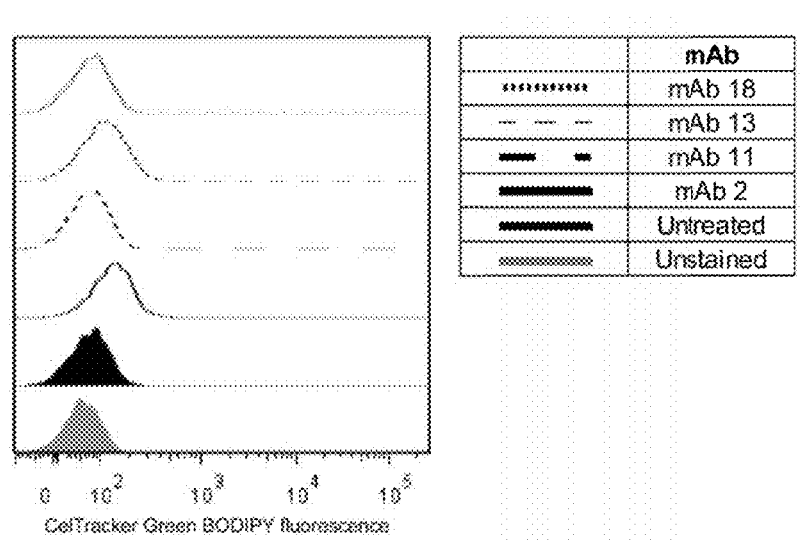
B)
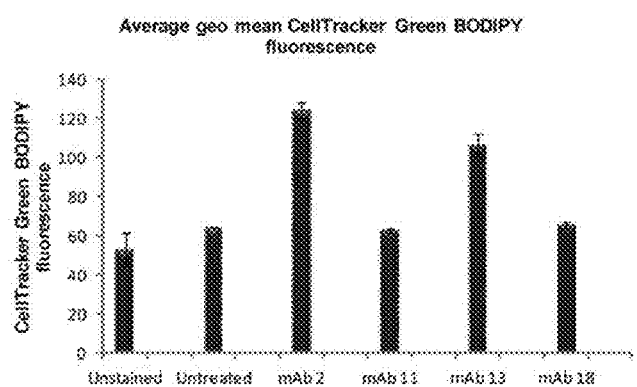
C)

FIG. 13

```
<------------------------------------------------ FR1 - IMGT
1               5                      10                      15
Q   V   Q   L   K   E   S   G   G       G   L   V   Q   P
cag gtg cag ctg aag gag tcc gga gga ... ggc ttg gta cag cct ------------------------------------------>
                20                      25                      30
G   G   S   L   T   L   S   C   A   T   S   G   F   T   F
ggg ggt tct ctg aca ctc tcc tgt gca act tct gga ttc acc ttc CDR1 - IMGT                    <------------------------------
                35                      40                      45
                        T   D   Y   Y   M   S   W   V   R   Q   P
... ... ... ... act gat tac tac atg agc tgg gtc cgc cag cct FR2 - IMGT ------------------------>                   CDR2
                50                      55                      60
P   G   K   A   L   E   W   L   A   F   I   R   N   K   A
cca gga aag gca ctt gag tgg ttg gct ttt atc aga aac aaa gct

- IMGT              <------------------------------
                65                      70                      75
K   G   Y   T   T   E   Y   N   A   S   V   R       G   R
aaa ggt tat aca aca gaa tac aat gca tct gtg agg ... ggt cgg -------------------------------- FR3 - IMGT --------------------
                80                      85                      90
F   T   I   S   R   D   N   S   Q   N   I   V   Y   L   Q
ttc acc atc tcc aga gat aat tcc caa aac atc gtc tat ctt caa ------------------------------------------>
                95                      100                     104
M   N   T   L   R   T   E   D   S   A   T   Y   Y   C   A
atg aac acc ctg aga act gag gac agt gcc act tat tac tgt gca CDR3 - IMGT
R   D   G   V   G   I   A   Y   W   G   Q   G   T   L   V
aga gat ggg gtg gga att gct tac tgg ggc caa ggg act ctg gtc T   V   S   A   A   K   T   T   P   P   S   V   Y   P   L
act gtt tct gca gcc aaa acg aca ccc cca tct gtc tat cca ctg A   P
gcc cct
```

FIG. 14

```
<-------------------------------------------------- FR1 - IMGT
 1             5              10             15
 S  I  V  M  T  Q  S  P  L  S  L  P  V  S  L
agc att gtg atg acc cag tct cca ctc tcc ctg cct gtc agt ctt -------------------------------------------->
              20             25             30
 G  D  Q  A  S  I  S  C  R  S  S  Q  S  L  E
gga gat caa gcc tcc atc tct tgc agg tct agt cag agc ctt gaa __ CDR1 - IMGT _____  <----------------------------
              35             40             45
 N  I     N  G  N  T  Y  L  N  W  Y  F  Q  K
aac att ... aat gga aac acc tat ttg aac tgg tac ttc cag aaa FR2 - IMGT ------------------------>  _____ CDR2
              50             55             60
 P  G  Q  S  P  Q  L  L  I  Y  R  V
cca ggc cag tct cca cag ctc ctg atc tac agg gtt ... ... ...

- IMGT _____  <-----------------------------------------
              65             70             75
                     S  N  R  V  S  G  V  L     D  R
... ... ... ... tcc aac cga gtt tct ggg gtc cta ... gac agg ---------------------------------- FR3 - IMGT ----------------
              80             85             90
 F  S  G  S  G           S  G  T  D  F  T  L  K
ttc agt ggt agt gga ... ... tca ggg aca gat ttc aca ctg aaa --------------------------------------------------->
              95             100            104
 I  T  R  V  E  A  E  D  L  G  V  Y  F  C  L
atc acc aga gtg gag gct gag gat ttg gga gtt tat ttc tgc ctc

_____ CDR3 - IMGT _____

Q  V  T  H  V  P  W  T  F  G  G  G  T  K  L
caa gtt aca cat gtc ccg tgg acg ttc ggt gga ggc acc aaa ctg E  I  K  R  A  D  A  A  P  T  K  S  I  S
gaa atc aaa cgg gct gat gct gca cca act aag tcc atc tcc
```

MAB 2 ANTI-MET ANTIBODY

CROSS-REFERENCE TO RELATED APPLICATIONS

This application is a U.S. National Stage Filing under 35 U.S.C. 371 from International Application No. PCT/SG2014/000144, filed on Mar. 28, 2014, and published as WO 2014/178791 A1 on Nov. 6, 2014, which claims the benefit of priority of Singapore patent application No. 201306428-2, filed Aug. 23, 2013, and Singapore patent application no. 201303329-5, filed Apr. 30, 2013 the contents of each of which are being hereby incorporated by reference in their entireties for all purposes.

FIELD OF THE INVENTION

The present invention lies in the field of immunology and relates to antibodies specifically binding to c-Met, fragments thereof, and uses thereof.

BACKGROUND OF THE INVENTION c-Met is a 190 kD tyrosine kinase receptor made up of an extracellular α-chain which is linked by a disulphide bond to a transmembrane β-chain. c-Met is synthesised as a 170 kD single polypeptide that is proteolytically cleaved to form the α-chain and the β-chain. The mature α-chain is 45 kD and constitutes part of the sema domain. The sema domain is a conserved domain shared by semaphorins and plexins. This domain adopts a seven-bladed beta-propeller structure which is important for homo-dimerisation. In c-Met, both the α-chain and the β-chain form the sema domain that is necessary and sufficient for receptor dimerisation and ligand binding.

Hepatocyte growth factor (HGF) is the only known c-Met ligand. Upon HGF binding, c-Met receptor dimerises on the cell surface which results in autophosphorylation of tyrosine residues in the kinase domain. Autophosphorylation is thought to induce a conformational change in c-Met, exposing the docking site in the carboxyl-terminal tail of c-Met. This results in transphosphorylation of tyrosine residues in c-Met docking site. The docking site becomes available for recruitment of adaptor and signalling molecules resulting in the activation of various signalling pathways including the AKT/PI3K, RAS/MAPK and STAT pathways.

Aberrant c-Met activation of c-Met signalling pathways correlates with hyperproliferation, tumour cell invasion, tumour angiogenesis and poor prognosis in various human cancers. In addition, c-Met signalling protects the tumour cell by inhibiting apoptosis and inducing resistance towards cancer therapy, thus hampering the efforts of tumour treatment. c-Met as a cancer prognosis marker and its involvement in cancer metastasis and drug resistance makes c-Met a very attractive drug target.

Various mechanisms have been used to inhibit c-Met activation. Small molecule kinase inhibitors such as the PHA-665752, AM7 and SU11274 were extremely successful in inhibiting c-Met activation. However, toxicity issues due to off-target effects of the small molecule inhibitors are of major concern. In addition, SU11274 was reported to be ineffective against specific c-Met mutations.

The use of U1snRNA/ribozyme has also been reported to downregulate the expression levels of c-Met/HGF. However this method is not feasible for cancer treatment due to drug delivery issues. U1snRNA/ribozyme has to be efficiently delivered into every tumour cell to be expressed in order to be effective.

The use of HGF and c-Met fragments, such as NK4 and decoy-Met respectively, to compete for Met-HGF interactions has been examined. These competitive inhibitors show efficient inhibition of c-Met activation in vivo xenograft models; however, their clinical utility has yet to be determined.

Many antibodies, such as Herceptin (clinically known as Trastuzamab), have been clinically successful. Herceptin is a chimeric antibody targeted against the tyrosine receptor kinase HER2, used for breast cancer treatment.

With the success of therapeutic antibodies, attempts have been made to develop therapeutic antibodies against the Met-HGF axis. Neutralising antibodies targeted against HGF aimed to block Met-HGF interaction were developed. c-Met binding to HGF was only blocked when a combination of two or three different anti-HGF antibodies were used. Five fully human anti-HGF antibodies targeted against the β-chain of HGF have been developed. These antibodies were successful in blocking Met-HGF interaction in U-87MG glioblastoma cells.

Developing therapeutic bivalent antibodies targeted against c-Met has been challenging. Two monoclonal antibodies (DO-24 and DN-30) against the extracellular domain of c-Met have previously been developed. Interestingly, both monoclonal antibodies act as an agonist rather than an antagonist and activate c-Met signalling in vivo. To avoid c-Met activation by bivalent monoclonal antibodies, a DN-30 Fab fragment was engineered. DN-30 Fab retained its high binding affinity towards c-Met but lost its agonist activity towards c-Met. DN-30 Fab efficiently inhibited c-Met signalling by causing c-Met ectodomain shedding and receptor down regulation.

The one-arm 5D5 antibody (MetMab or clinically known as Onartuzumab) is a monovalent chimeric antibody targeted against c-Met. Like DN-30, bivalent 5D5 antibody became an antagonist when converted to a monovalent Fab. In contrast to Fab DN-30, MetMab acts as an antagonist by competing with HGF for c-Met binding and causes c-Met internalisation and down-regulation.

Thus, there is a need to provide new antagonist antibodies binding to c-Met that overcome, or at least ameliorate, one or more of the disadvantages described above.

SUMMARY OF THE INVENTION

Described below are antibodies against the α-chain of human c-Met. The development of a panel of bivalent anti-Met murine monoclonal antibodies, raised against the α-chain of human c-Met. These antibodies were characterised by Western blotting, immunoprecipitation, flow cytometry, epitope mapping and agonist/antagonist activity towards c-Met. Surprisingly, none of these antibodies were c-Met agonist. Two antibodies, mAb 2 and 13, showed the strongest binding to native c-Met by flow cytometry but work poorly to detect denatured c-Met on Western blots. mAb 2 was the most effective in reducing cell proliferation. Further analysis of mAb 2 on flow cytometry showed that its binding to c-Met on live cells is temperature sensitive. Detailed mapping of mAb 2 epitope revealed that part of mAb 2 epitope is buried within c-Met.

Thus, in a first aspect, there is provided an antibody specifically binding an epitope comprised in the α-chain of c-Met.

In a second aspect, there is provided nucleic acid encoding an antibody as described herein, wherein the heavy chain of the antibody comprises or consists of the sequence as shown in SEQ ID NO: 1.

In a third aspect, there is provided a pharmaceutical composition comprising or consisting of an antibody as described herein.

In a fourth aspect, there is provided a method of treating and/or preventing cancer comprising administration of a therapeutically effective, amount of an antibody as described herein.

In a fifth aspect, there is provided a method of diagnosing cancer comprising detection of aberrant expression of c-Met by administering an antibody as described herein for detecting c-Met.

In a sixth aspect, there is provided the use of an antibody disclosed herein in the manufacture of a medicament for treating and/or preventing cancer.

In a seventh aspect, there is provided the use of an antibody disclosed herein for detecting cells with aberrant c-Met expression.

In an eight aspect, there is provided the use of an antibody disclosed herein as cancer prognosis marker.

BRIEF DESCRIPTION OF THE DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

FIG. 4 shows representative signals from flow cytometry analysis of SNU-5 cells treated with anti-α-chain c-Met monoclonal antibodies. Purified monoclonal antibodies (1 μg/mL) were incubated with live SNU-5 cells. Bound antibodies were detected using FITC-conjugated secondary antibodies before the cells were passed through a flow cytometer. A shift in FITC intensity indicates monoclonal antibodies binding to SNU-5 cells.

FIG. 6 is a pair of bar graphs showing the effects of purified anti-α-chain c-Met monoclonal antibodies on SNU-5 cell viability and caspase activation. 10 μg/mL of monoclonal antibody were added to SNU-5 cells in the presence of serum containing media. Cells were incubated for 72 hrs before (A) cell viability and (B) caspase activation were tested. SU11274 (5 μM) was used as control.

FIG. 7 is a series of assays demonstrating the effect of mAb 2 and mAb 13 on cell growth. 10 μg/mL of monoclonal antibody were incubated with SNU-5 cells in the presence of serum containing media. A) is a bar graph showing cell growth of SNU-5 cells. 72 hrs post monoclonal antibody treatment, cells were harvested and counted using the automated ADAM cell counter (Digital Bio). DAY 0: number of cell seeded for the assay. B & C) SNU-5 cells were stained with 5 μM CellTracker Green BODIPY dye before incubating with monoclonal antibody for 6 days. Fresh media containing 10 μg/mL of monoclonal antibody was added to the cells on alternate days. Cells were harvest and Cell- Tracker Green BODIPY fluorescence retention was analysed by flow cytometry. B) Histogram representation of fluorescent cells treated with respective monoclonal antibody. C) CellTracker Green BODIPY fluorescence intensity of monoclonal antibody treated cells was recorded by flow cytometry. Experiment was performed in duplicates. Average geometric mean fluorescence was obtained and plotted.

FIG. 11 shows under C) presents image of a Western Blot showing analysis of human c-Met using mAb 2. mAb 2 was purified from mouse ascites and tested for reactivity against full length c-Met in whole cell lysates. 50 µg of whole cell lysate was obtained from untransfected NIH3T3 mouse cells (UT), NIH3T3 mouse cells transfected with full length human c-Met (Met), U-87 MG human glioblastoma cells and T47D human breast cancer cells. mAb 2 was used at a concentration of 1 µg/mL. 10 ng of purified α-chain was used as positive control. Upper arrows indicate c-Met precursor (170 kD). Lower arrows indicate purified α-chain. Molecular weights are noted aside, in kilodaltons.

FIG. 11 shows under D) is a histogram plot showing a flow cytometry analysis of SNU-5 human gastric cells by anti-Met antibodies. SNU-5 cells express high levels of c-Met. 1 µg/mL of anti-Met antibodies were incubated with live SNU-5 cells. Bound anti-Met antibodies were detected using FITC-conjugated secondary antibodies before passing the cells through a flow cytometer. Secondary antibody only was used as control. A right shift in FITC intensity indicates monoclonal antibodies binding to SNU-5 cells. mAb 2 and mAb 13 bound to live SNU-5 strongly.

FIG. 11 shows under E) is a, bar graph showing the effect of mAb 2 and mAb 13 on cell growth. 10 µg/mL of mAb was incubated with SNU-5 cells in the presence of serum containing media. 72 hrs post mAb treatment, cells were harvested and counted using the automated ADAM cell counter (Digital Bio). DAY 0: number of cell seeded for the assay.

FIG. 13 is the nucleotide (SEQ ID NO:17) and protein sequence (SEQ ID NO:9) of mAb 2 heavy chain. Alignment, nucleotide translation and CDR. predictions were performed using IMGT/V-QUEST software available on the IMGT (The international immunogenetics information system) webpage.

FIG. 14 presents the nucleotide (SEQ ID NO:16) and protein sequence (SEQ ID NO:8) of mAb 2 light chain. Alignment, nucleotide translation and CDR predictions were performed using IMGT/V-QUEST software available on the IMGT (The international immunogenetics information system) webpage.

DETAILED DESCRIPTION OF THE PRESENT INVENTION

Figure 1:
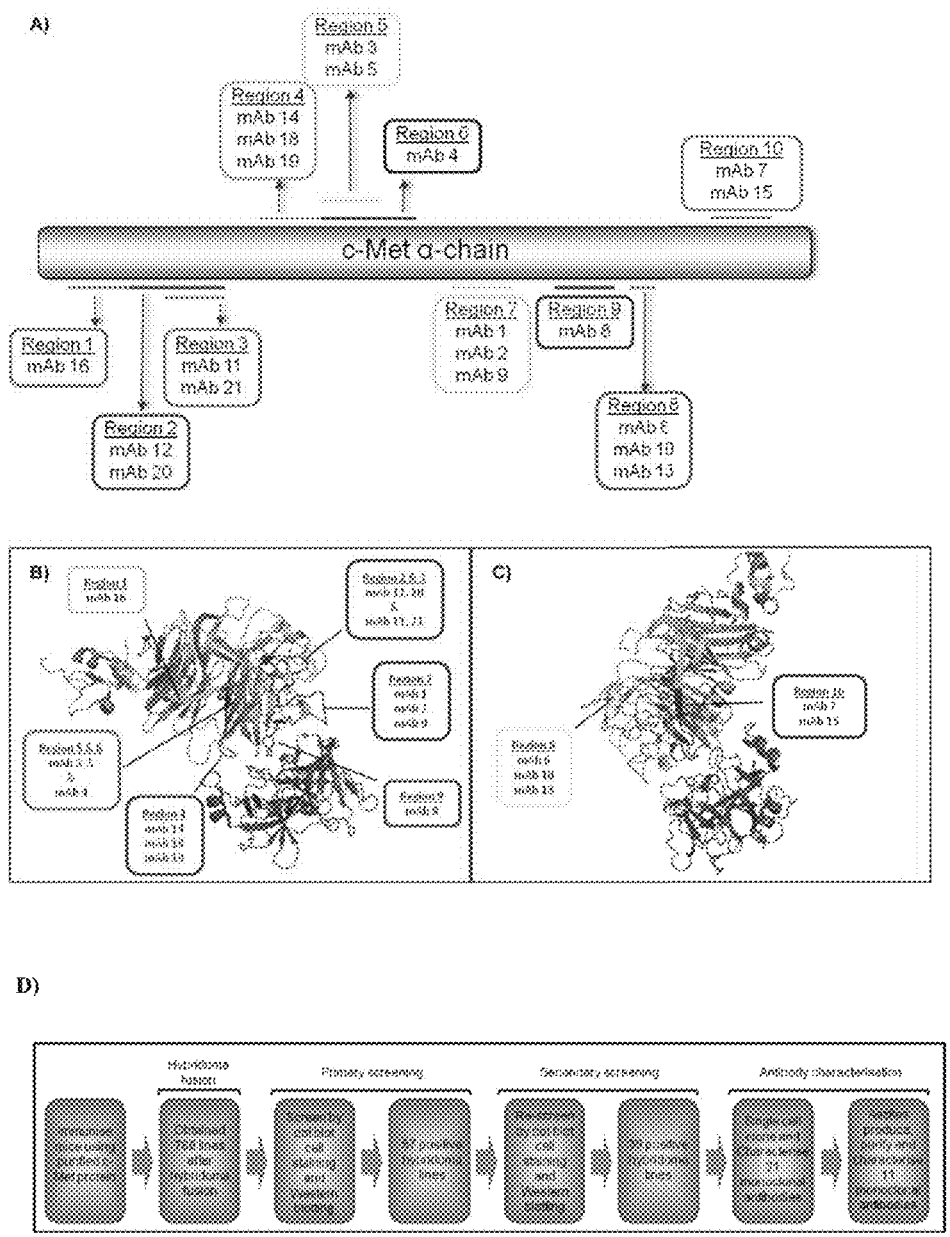
FIG. 1 is a cartoon illustrating the mapping of the anti-α-chain c-Met monoclonal antibody epitope mapping. A) Schema of antibody binding regions. Pepscan, an ELISA-based assay, was used to determine the binding region of 21 monoclonal supernatants. Consecutive overlapping peptides that span the entire c-Met α-chain were synthesised and coated in 96-wells. To determine the region of antibody binding on the α-chain, monoclonal cell supernatants were added to each peptide. Antibody binding results in a colourmetric reaction which is analysed by absorbance reading at 450 nM. The epitope of the antibodies were categorised into regions. Antibodies that share the same binding region are indicated. Figure not drawn to scale. B & C) Mapping of antibody binding regions to the crystal structure of c-Met. Crystal structure of c-Met extracellular domain (amino acid residues 25-567), binding to HGF β-chain. Crystal structure was obtained from Protein Data Bank (PDB), accession number 1SHY. c-Met is highlighted in light grey and HGF in dark grey. The protein complex is shown from two different viewpoints (B) and (C) to allow visualisation of the different antibody binding regions in relation to ligand-receptor interaction site. (D) is a schematic diagram illustrating the outline of monoclonal antibody screening. 768 cell lines were screened for the production of anti-α-chain antibodies after hybridoma fusion. 57 lines were found to express anti-α-chain c-Met antibodies in the primary screen. These lines were expanded and tested again for the production of anti-α-chain antibodies in the secondary screen. 39 lines were observed to stably express anti-α-chain antibodies. 21 lines were selected for single-cell cloning. These antibodies were then characterised for region of binding, isotype subclasses and functionality on Western blots. Based on these assays, 11 clones were selected for ascites production. Monoclonal antibodies were purified from ascites and characterised further.

Before the present antibodies, fragments and uses thereof are described, it is to be understood that this invention is not limited to particular peptides, methods, uses and experimental conditions described, as such peptides, methods, uses and conditions may vary. It is also to be understood that the terminology used herein is for purposes of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Any methods and materials similar or equivalent to those described herein can be used in the practice or testing of the invention, as it will be understood that modifications and variations are encompassed within the spirit and scope of the instant disclosure.

In the present invention, antibodies peptides have been designed that specifically bind an epitope in the α-chain of c-Met. Western blotting, immunoprecipitation, flow cytometry, epitope mapping, agonist/antagonist activity towards c-Met and crystal structure were used to characterize a panel of bivalent anti-Met murine monoclonal antibodies, raised against the α-chain of human c-Met. The inventors found that the antibodies described herein are c-Met antagonist contrary to previously described therapeutic bivalent antibodies targeted against c-Met. Antibodies of the invention are also shown to be effective in reducing cell proliferation.

The term "c-Met" or "c-Met protein" as used herein is meant a 190 kD tyrosine kinase receptor (SEQ ID NO: 1) made up of an extracellular α-chain (SEQ ID NO: 58) which is linked by a disulphide bond to a transmembrane β-chain (SEQ ID NO: 59). c-Met is synthesised as a 170 kD single polypeptide that is proteolytically cleaved to form the α-chain and the β-chain. The mature α-chain is 45 kD and constitutes part of the sema domain. The sema domain is a conserved domain shared by semaphorins and plexins. This domain adopts a seven-bladed beta-propeller structure which is important for homo-dimerisation. In c-Met, both the α-chain and the β-chain form the sema domain that is necessary and sufficient for receptor dimerisation and ligand binding. The 140 kD mature β-chain consists of an extracellular domain, a transmembrane domain and a cytoplasmic domain. The extracellular portion of the β-chain makes up the remainder of the sema domain. The cytoplasmic portion of c-Met β-chain contains the juxtamembrane region followed by a kinase domain and a carboxyl-terminal tail. The carboxyl-terminal tail is essential for c-Met downstream signaling as it contains the docking site for signaling and adapter proteins that bind to c-Met.

The term "extracellular region" as defined herein indicates, with respect to a transmembrane protein, the region of the protein exposed to the exterior of the cell. The α-chain of c-Met is entirely extracellular, that is the α-chain of c-Met does not possess a transmembrane domain.

c-Met is the receptor that binds HGF (Hepatocyte growth factor) and as a result initiates a signal transduction pathway within the cell. c-Met proteins may also include variants. c-Met proteins may also include fragments, such as the extracellular domain that don't have all or part of the transmembrane and/or the intracellular domain, as well as fragments of the extracellular domain. The cloning, characterization, and preparation of c-Met have previously been described. The amino acid sequence of the human c-Met is shown in SEQ ID NO: 1. Soluble forms of human c-Met useful in the methods of the present invention include the extracellular domain or the mature form lacking the signal peptide or a fragment of the extracellular domain that retains the capacity to bind HGF. The term "c-Met" also includes post-translational modifications of the c-Met amino acid sequence. Post-translational modifications include, but are not limited to, N- and O-linked glycosylation.

The present invention provides antibodies that specifically bind an epitope comprised in the α-chain of c-Met. Examples of antibodies comprise peptides and/or polypeptides (that optionally include post-translational modifications) that specifically bind an epitope comprised in the α-chain of c-Met. Examples of antibodies comprise antibodies and fragments thereof, as variously defined herein, that specifically bind an epitope comprised in the α-chain of c-Met. Examples of the invention include antibodies that specifically bind to human c-Met and inhibit HGF from binding and activating c-Met.

The term "antibody" (Ab) is used in the broadest sense and specifically covers monoclonal antibodies (including full length monoclonal antibodies), polyclonal antibodies, monospecific antibodies, multispecific antibodies (e.g., bispecific antibodies), and antibody fragments as long as they still exhibit the desired biological activity. In the context of the present invention "antibody" refers to an immunoglobulin molecule, a fragment of an immunoglobulin molecule, or a derivative of either thereof, which has the ability to specifically bind to an antigen under typical physiological conditions with a half-life of significant periods of time, such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to recruit an effector activity). The variable regions of the heavy and light chains of the immunoglobulin molecule contain a binding domain that interacts with an antigen. The constant regions of the antibodies (Abs) may mediate the binding of the immunoglobulin to host tissues or factors, including various cells of the immune system (such as effector cells) and components of the complement system such as Clq, the first component in the classical pathway of complement activation. A c-Met antibody may also be a bispecific antibody, diabody, or similar molecule. Indeed, bispecific antibodies, diabodies, and the like, provided by the present invention may bind any suitable target in addition to a portion of c-Met. As indicated above, the term antibody herein, unless otherwise stated or clearly contradicted by context, includes fragments of an antibody that are antigen-binding fragments, i.e., retain the ability to specifically bind to the antigen. It has been shown that the antigen-binding function of an antibody may be performed by fragments of a full-length antibody. Examples of antigen-binding fragments encompassed within the term "antibody" include (i) a Fab' or Fab fragment, a monovalent fragment consisting of the $V_L$, $V_H$, $C_L$ and $C_H1$ domains, or a monovalent antibody; (ii) F(ab')2 fragments, bivalent fragments comprising two Fab fragments linked by a disulfide bridge at the hinge region; (iii) a Fd fragment consisting essentially of the $V_H$ and $C_H1$ domains; (iv) a Fv fragment consisting essentially of the $V_L$ and $V_H$ domains of a single arm of an antibody, (v) a dAb fragment, which consists essentially of a $V_H$ domain and also called domain antibodies; (vi) camelid or nanobodies and (vii) an isolated complementarity determining region (CDR). Furthermore, although the two domains of the Fv fragment, $V_L$ and $V_H$, are coded for by separate genes, they may be joined, using recombinant methods, by a synthetic linker that enables them to be made as a single protein chain in which the $V_L$ and $V_H$ regions pair to form monovalent molecules (known as single chain antibodies or single chain Fv (scFv)). Such single chain antibodies are encompassed within the term antibody unless otherwise noted or clearly indicated by context. Although such fragments are generally included within the meaning of antibody, they collectively and each independently are unique features of the present invention, exhibiting different biological properties and utility. These and other useful antibody fragments in the context of the present invention, as well as bispecific formats of such fragments, are discussed further herein. It also should be understood that the term antibody, unless specified otherwise, also includes polyclonal antibodies, monoclonal antibodies (mAbs), antibody-like polypeptides, such as chimeric antibodies and humanized antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype.

The term "monovalent antibody" means in the context of the present invention that an antibody molecule is capable of binding a single molecule of the antigen, and thus is not able of antigen crosslinking.

The term "monoclonal antibody" refers to an antibody composition having a homogenous (essentially identical) antibody population. The term is not limited regarding the species, e.g., human, murine, mouse, or canine or the source of the antibody, nor is it limited by the manner in which it is made. For example, the term includes monoclonal antibodies produced by a methodology other than hybridoma which results in monoclonal antibodies no matter how subcategorized, e.g., hybrid, altered, chimeric, or humanized. Further, the term includes variants that naturally arise during the production of monoclonal antibodies. The term includes whole immunoglobulins. The term "humanized antibody" as used herein refers to an engineered antibody that typically comprises the variable region of a non-human (e.g., murine) antibody, i.e., a chimeric antibody, or at least the complementarity determining regions (CDRs) thereof, and the remaining immunoglobulin portions derived from a human antibody. Procedures for the production of chimeric antibody and further engineered monoclonal antibodies include those described in the art. Such humanized antibodies may be prepared by known techniques and offer the advantage of reduced immunogenicity when the antibodies are administered to humans.

Thus, the terms "c-Met antibody" or "anti-c-Met antibody" as used herein refer to an antibody as defined above that is capable of binding to the c-Met protein with higher affinity than to other proteins. The "c-Met antibody" is an antibody that was raised against a c-Met protein or fragment thereof as defined above and herein thereafter.

The term "epitope" as defined herein refers to a site on an antigen at which an antibody can bind, the molecular arrangement of the site determining the specific combining antibody. It is also called antigenic determinant. Epitopes usually consist of surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. The epitope may comprise amino acid residues directly involved in the binding (also called immunodominant component of the epitope) and other amino acid residues, which are not directly involved in the binding, such as amino acid residues which are effectively blocked by the specifically antigen binding peptide (in other words, the amino acid residue is within the footprint of the specifically antigen binding peptide).

The antibodies of the invention specifically bind to an epitope comprised in the α-chain of c-Met. The expression "specifically binding" as used herein refers to a binding reaction between an antibody, including the antibodies of the present invention, and a protein, e.g., a target receptor, which is determinative of the presence of the protein in a heterogeneous population of proteins and other chemical species. More specifically as used herein the phrase "specifically binding" means that the antibody preferentially binds c-Met over other proteins. In some embodiments "specifically binds" means that the c-Met antibodies have a higher affinity for c-Met than for other proteins. For example, the equilibrium dissociation constant is $<10^{-7}$ to $10^{-11}$ M, or $<10^{-8}$ to $<10^{-10}$ M, or $<10^{-9}$ to $<10^{-10}$ M. Thus, under designated immunoassay conditions, the antibodies bound to a particular protein do not bind in a significant amount to other proteins present in a sample. Specifically binding to a protein under such conditions may require an antibody that is selected for its specificity for that particular protein. A variety of immunoassay formats may be used to select antibodies that selectively bind with a particular protein. For example, solid-phase ELISA immunoassays are routinely used to select antibodies selectively immunoreactive with a protein.

The term "immunoglobulin" refers to a class of structurally, related glycoproteins consisting of two pairs of polypeptide chains, one pair of light (L) low molecular weight chains and one pair of heavy (H) chains, all four interconnected by disulfide bonds. The structure of immunoglobulins has been well characterized. Briefly, each heavy chain typically is comprised of a heavy chain variable region (abbreviated herein as $V_H$ or VH) and a heavy chain constant region. The heavy chain constant region typically is comprised of three domains, $C_H1$, $C_H2$, and $C_H3$. Each light chain typically is comprised of a light chain variable region (abbreviated herein as $V_L$ or VL) and a light chain constant region. The light chain constant region typically is comprised of one domain, $C_L$. The $V_H$ and $V_L$ regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each $V_H$ and $V_L$ is typically composed of three CDRs and four FRs, arranged from amino-terminus to carboxy-terminus in the following order: FR1, CDR1, FR2, CDR2, FR3, CDR3, FR4. Unless otherwise stated or contradicted by context, CDR sequences herein are identified according to IMGT (The international immunogenetics information system) rules.

However, the numbering of amino acid residues in an antibody sequence can also be performed by the method described in Kabat et al., Sequences of Proteins of Immunological Interest, 5th Ed. Public Health Service, National Institutes of Health, Bethesda, Md. (1991) (phrases such as "variable domain residue numbering as in Kabat", "Kabat position" or "according to Kabat" herein refer to this numbering system). Particularly, for numbering of amino acids in the constant region, the EU index numbering system according to Kabat et al, supra, can be used. The Kabat numbering of residues may be determined for a given antibody by alignment at regions of homology of the sequence of the antibody with a "standard" Kabat numbered sequence.

As used herein, "isotype" refers to the immunoglobulin class (for instance IgG 1, IgG2, IgG3, IgG4, Ig D, IgA, Ig E, or Ig M) that is encoded by heavy chain constant region genes. The structure of a naturally occurring, intact antibody, or immunoglobulin, includes four polypeptides: two full-length light chains and two full-length heavy chains, with each light chain linked to a heavy chain by disulfide bonds. Each heavy chain has two regions, a constant region and a variable region There are five isotypes for heavy chain constant regions, gamma (γ), mu (μ), alpha (α), delta (δ), or epsilon (ε), which can be further categorized by subtypes as gamma 1 (γ1), gamma 2 (γ2), gamma 3 (γ3), gamma 4 (γ4), alpha 1 (α1), or alpha 2 (α2). Similarly, each light chain has two regions, a constant region and a variable region. The light chain constant region is of either a kappa (κ) or lambda (λ) type. The variable regions differ in sequence among antibodies and are used in the binding and specificity of a given antibody to its particular antigen.

It is understood that when reference is made to the various examples of the c-Met antibodies described herein, that it also encompasses c-Met antibodies fragments thereof. A c-Met antibody fragment comprises any of the antibody fragments or domains described herein that retains the ability to specifically bind to c-Met.

In embodiments where the antibody is used for therapeutic applications, one characteristic of a c-Met antibody is that it can inhibit binding of HGF and one or more biological activities of, or mediated by, c-Met. Such antibodies are considered neutralizing antibodies because of their capacity to inhibit HGF from binding and causing c-Met signalling and/or biological activity. In this case, an antibody specifically binds c-Met and inhibits binding of HGF to c-Met from anywhere between 10 to 100%, such as by at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% or more (for example by measuring binding in an in vitro competitive binding assay as described herein). For example, c-Met antibodies may be tested for neutralizing ability by testing with any suitable assay known in the art. Examples, for illustrative purposes only, of additional biological activity of c-Met (e.g., assay readouts) to test for inhibition of c-Met signalling and/or biological activity include in vitro and/or in vivo measurement of cell scatter in cell scatter assays.

As a general structure, the antibodies of the invention comprise (a) a scaffold, and (b) one or a plurality of CDRs. A "complementary determining region" or "CDR," as used herein, refers to a binding protein region that constitutes the major surface contact points for antigen binding. Embodiments of the invention include one or more CDRs embedded in a scaffold structure of the antibody. The scaffold structure of the antibodies may be the framework of an antibody, or fragment or variant thereof, or may be completely synthetic in nature. Examples of various scaffold structures of the antigen binding proteins of the invention are further described hereinbelow.

The antibodies of the invention include scaffold regions and one or more CDRs. An antigen binding protein of the invention may have between one and six CDRs (as typically do naturally occurring antibodies), for example, one heavy chain CDR1 ("H-CDR1"), and/or one heavy chain CDR2 ("H-CDR2"), and/or one heavy chain CDR3 ("H-CDR3"), and/or one light chain CDR1 ("L-CDR1"), and/or one light chain CDR2 ("L-CDR2"), and/or one light chain CDR3 ("L-CDR3").

The term "naturally occurring" as used throughout the specification in connection with biological materials such as peptides, polypeptides, nucleic acids, host cells, and the like, refers to materials which are found in nature. In naturally occurring antibodies, a H-CDR1 typically comprises about five (5) to about seven (7) amino acids, H-CDR2 typically comprises about sixteen (16) to about nineteen (19) amino acids, and H-CDR3 typically comprises about three (3) to about twenty five (25) amino acids. L-CDR1 typically comprises about ten (10) to about seventeen (17) amino acids, L-CDR2 typically comprises about seven (7) amino acids, and L-CDR3 typically comprises about seven (7) to about ten (10) amino acids. Specific CDRs of the various antibodies of the invention are provided in TABLE 1 and the Sequence Listing.

TABLE 1

| mAb 2 CDR sequence | | | | |
|---|---|---|---|---|
| | Nucleotide sequence | SEQ ID NO: | Protein sequence | SEQ ID NO: |
| Heavy chain | | | | |
| CDR1 | gga ttc acc ttc act gat cac tac atg agc | 18 | GFTFTDHYMS | 2 |
| CDR2 | ttt atc aga aac aaa gct aaa ggt tat aca aca gaa | 19 | FIRNKAKGYTTE | 3 |
| CDR3 | gca aga gat ggg gtg gga att gct tac | 20 | ARDGVGIAY | 4 |
| Light chain | | | | |
| CDR1 | agg tct agt cag agc ctt gaa aac att aat gga aac acc tat ttg aac | 21 | RSSQSLENINGNTYLN | 5 |
| CDR2 | agg gtt tcc aac cga gtt tct | 22 | RVSNRVS | 6 |
| CDR3 | ctccaa gtt aca cat gtc ccg tgg acg | 23 | LQVTHVPWT | 7 |

The term "antagonize" or "antagonizing" as used herein refers to blocking, impeding, preventing, reducing, inhibiting, lessening or in some way interfering with the biological activity of the associated protein of interest such as a target receptor. The term "antagonist" or "antagonistic" refers to a compound that antagonizes a biological activity of the protein of interest.

As used herein, "internalization", when used in the context of a c-Met antibody includes any mechanism by which the antibody is internalized into a c-Met-expressing cell from the cell-surface and/or from surrounding medium, e.g., via endocytosis. The internalization of an antibody can be evaluated using a direct assay measuring the amount of internalized antibody, or an indirect assay where the effect of an internalized antibody-toxin conjugate is measured.

The present invention also provides antibodies comprising functional variants of the $V_L$ region, $V_H$ region, or one or more CDRs of the antibodies of the examples. A functional variant of a $V_L$, $V_H$, or CDR used in the context of a c-Met antibody still allows the antibody to retain at least a substantial proportion (at least about 50%, 60%, 70%, 80%, 90%, 95% or more) of the affinity/avidity and/or the specificity/selectivity of the parent antibody and in some cases such a c-Met antibody may be associated with greater affinity, selectivity and/or specificity than the parent antibody.

Such functional variants typically retain significant sequence identity to the parent antibody. The percentage of identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The percent identity between two nucleotide or amino acid sequences may e.g. be determined using algorithm known in the art. In addition, the percent identity between two amino acid sequences may be determined using algorithm known to the skilled artisan.

Exemplary, variants include those which differ from a parent at one or more "variant" amino acid positions, denoted "*" in the corresponding consensus sequence.

Alternatively or additionally, the sequence of epitopes variants may differ from the sequence of the consensus epitope sequences mainly by conservative substitutions; for instance at least 10, such as at least 9, 8, 7, 6, 5, 4, 3, 2 or 1 of the substitutions in the variant are conservative amino acid residue replacements.

In the context of the present invention, conservative substitutions may be defined by substitutions within the classes of amino acids reflected in the following table:

Amino acid residue classes for conservative substitutions

| | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

The terms "agonize," "agonist" and "agonistic" when used herein refer to or describe a molecule which is capable of, directly or indirectly, substantially inducing, promoting or enhancing cytokine biological activity or cytokine receptor activation.

In an embodiment, the antibody as disclosed herein may specifically bind an epitope comprising or consisting of the sequence IEE or CPD; or IEE or CPDC; or IEE and CPD, or IEE and CPDC (SEQ ID NO: 60). In a further variation, the epitope comprises or consists of the amino acid sequences ****IFE*CPD (SEQ ID NO: 12) or *IEE*CPDC** (SEQ ID NO: 13). As indicated above, "*" denotes any amino acid.

In a further variation the epitope comprised in the α-chain of c-Met to which the antibody of the invention specifically binds, comprises or consists of the sequence ****IEE*CPD as defined above that is C***P*IEEPCPD (SEQ ID NO: 14). In a further variation, the sequence C*P*IEEP**CPD is CIFSPQIEEP-SQCPD (SEQ ID NO: 16).

In another embodiment, the amino acid sequence of the epitope comprises or consists of *IEE*CPDC** is *IEEPCPDC** (SEQ ID NO: 15). In a further variation the amino acid sequence of the epitope is QIEEPSQCPD-CVVSA (SEQ ID NO: 17).

In some variations, the c-Met protein from which the epitope is derived may include regarding the species, but is not limited to, human, murine, equine, bovine, feline, ovine or canine or the source of the antibody, nor is it limited by the manner in which it is made. In some variations, the c-Met protein is human. In some variations, the α-chain of the human c-Met is prokaryotically expressed, for example using a baculoviral expression vector. For example, the Baculovirus Expression System may be used to express the α-chain of the human c-Met that was previously cloned in an optimized expression vector. The expression vector may be optimized for the expression and purification of the α-chain of the human c-Met in insect cells. Cloning, expression and purification of proteins or polypeptides are well documented and known in the art. Example, for illustrative purposes only, is given in Example 2 below.

The antibody as disclosed herein is not limited regarding the species, e.g., human, murine, equine, bovine, feline, ovine or canine or the source of the antibody, nor is it limited by the manner in which it is made. For example, the antibody includes, but is not limited to, a monoclonal antibody, a polyclonal antibody, a monospecific antibody, a multispecific antibody (e.g., bispecific antibody), and an antibody fragment as long as they still exhibit the desired biological activity. In a further embodiment, the c-Met antibody as disclosed herein is a monoclonal or polyclonal antibody. In some variations, the antibody as disclosed herein is a murine antibody. In further variations, the c-Met antibody is a murine monoclonal antibody.

In some embodiments, the antibody may include, but is not limited to, a humanized antibody, a chimeric antibody, a recombinant antibody, a single chain antibody, a diabody, a triabody, a tetrabody, a Fab fragment, a F(ab')2 fragment, an IgD antibody, an IgE antibody, an IgM antibody, an IgG1 antibody, an IgG2 antibody, an IgG3 antibody, and an IgG4 antibody. In some embodiments, the antibody is a chimeric antibody.

In certain embodiments, the CDRs include no more than one, two, three, four, five, or six amino acid additions, deletions, or substitutions from a H-CDR1 (i.e., CDR1 of the heavy chain, etc.), H-CDR2, H-CDR3, L-CDR1 (i.e., CDR1 of the light chain, etc.), L-CDR2, and L-CDR3, and fragments, derivatives, muteins, and variants thereof.

Examples of the invention include antibodies comprising a heavy chain variable region comprising at least one, or at least two or all of a heavy chain CDR1 (GFTFTDHYMS; SEQ ID NO: 2), CDR2 (FIRNKAKGYTTE; SEQ ID NO: 3) or CDR3 (ARDGVGIAY; SEQ ID NO: 4).

Examples of the invention include antibodies comprising a light chain variable region comprising at least one, or at least two or all of a light chain CDR1 (RSSQSLENINGN-
TYLN; SEQ ID NO: 5), CDR2 (RVSNRVS; SEQ ID NO: 6)
or CDR3 (LQVTHVPWT; SEQ ID NO: 7).

Examples of the invention include the antibody as described herein wherein the antibody comprises an amino acid sequence of at least one, at least two, at least three, at least four, at least five or all of the following: a heavy chain CDR1 (SEQ ID NO:2), CDR2 (SEQ ID NO:3), CDR3 (SEQ ID NO:4) and a light chain CDR1 (SEQ ID NO:5), CDR2 (SEQ ID NO:6), CDR3 (SEQ ID NO:7) of antibody mAb 2.

In other embodiments, the heavy and light chain variable domains of the antibodies are defined by having a certain percent identity to a reference heavy and/or light chain variable domain. For example, the antibody comprises A) a heavy chain variable domain amino acid that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain amino acid sequence of SEQ ID NO: 8; and B) a light chain variable, domain amino acid that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain amino acid sequence selected from the group consisting of SEQ ID NO:9.

Examples of the invention include antibodies comprising a heavy chain variable region of SEQ ID NO: 8 and/or a light chain variable region of SEQ ID NO: 9 having no more than one, two, three, four, five, or six amino acid additions, deletions, or substitutions. In yet another embodiment, the antibody has a heavy chain of SEQ ID NO: 8 or a sequence which is at least 95%, or 96%, or 97%, or 98% identical to SEQ ID NO: 8. In a further embodiment, the antibody has a light chain of SEQ ID NO: 9 or a sequence which is at least 95%, or 96%, or 97%, or 98% identical to SEQ ID NO: 9

Variations of the invention include antibodies comprising a light chain variable region of SEQ ID NO: 9. Examples of the invention include antibodies comprising a light chain variable region of SEQ ID NO: 9 having no more than one, two, three, four, five, or six amino acid additions, deletions, or substitutions. In an embodiment, the antibody as disclosed herein comprises a light chain variable region of SEQ ID NO: 8 or a sequence defined by having a certain percent identity to a reference light chain variable domain. For example, the antibody comprises a light chain variable domain amino acid of that is of SEQ ID NO: 8 or which is at least 80%, 81%, 82%, 83%, 84%, 85%, 86%, 87%, 88%, 89%, 90%, 91%, 92%; 93%, 94%, 95%, 96%, 97%, 98%, or 99% identical to a heavy chain amino acid sequence of SEQ ID NO:8. In yet another embodiment, the antibody has a heavy chain of SEQ ID NO: 8 or a sequence which is at least 95%, or 96%, or 97%, or 98% identical to SEQ ID NO: 8.

In some embodiments, the antibody comprises an amino acid sequence selected from the group consisting of:
A. a. a light chain variable domain sequence that is at least 80% identical to a light chain variable domain sequence of Ab2$_L$ (SEQ ID NO:9);
  b. a heavy chain variable domain sequence that is at least 80% identical to a heavy chain variable domain sequence of Ab2$_H$ (SEQ ID NO:8); or
  c. the light chain variable domain of (a) and the heavy chain variable domain of (b); and
B. a light chain CDR1, CDR2, CDR3 and a heavy chain CDR1, CDR2, CDR3 that differs by no more than a total of three amino acid additions, substitutions, and/or deletions in each CDR from the following sequences:
  a. a light chain CDR1 (SEQ ID NO:5), CDR2 (SEQ ID NO: 6), CDR3 (SEQ ID NO:7) and a heavy chain CDR1 (SEQ ID NO:2), CDR2 (SEQ ID NO:3), CDR3 (SEQ ID NO:4) of antibody Ab2; wherein said antibody specifically binds an epitope comprised in the α-chain of c-Met.

In another embodiment, the antibody as defined above may comprise an amino acid sequence having a light chain variable domain and a heavy chain variable domain of Ab2$_L$/Ab2$_H$ (SEQ ID NO:9/SEQ ID NO:8); wherein said antibody specifically binds an epitope comprised in the α-chain of c-Met.

In yet another embodiment, the antibody as described above comprises an amino acid sequence having a light chain CDR1 (SEQ ID NO: 5), CDR2 (SEQ ID NO:6), CDR3 (SEQ ID NO: 7) and a heavy chain CDR1 (SEQ ID NO:2), CDR2 (SEQ ID NO:3), CDR3 (SEQ ID NO:4) of antibody Ab2; wherein said antibody specifically binds an epitope comprised in the α-chain of c-Met.

In some embodiments, the antibody of the present invention may be coupled to an agent. The antibody or fragments thereof as disclosed herein may be conjugated, fused or coupled to the agent. The conjugation of the antibody may be achieved through methods known to those skilled in the art. The conjugation may include linkers and/or spacers. For example, Trastuzumab-DM1 (T-DM1; trastuzumab emtansine) is composed of the humanized antibody trastuzumab and DM1, a maytansinoid derivative, linked with a non-reducible thioether linker, N-succinimidyl-4-(N-maleimidomethyl)-cyclohexane-1-carboxylate (SMCC, designated MCC after conjugation). Maytansinoids are natural products that are potent antimitotic agents, which like the *vinca* alkaloids prevent microtubule assembly.

The linker is crosslinked to the antibody for proper drug delivery to the intended cellular compartment. Antibody-Drugs Conjugates are constructed through the reaction of drugs or chemical crosslinking reagents with solvent accessible reactive amino acids such as lysine and cysteine on the antibody. In some examples, the linkers may be cleavable, such as peptide, hydrazone, or disulfide linkers or non-cleavable, such as thioether. For example, Azide-Alkyne "click" bioconjugation chemistry may be used to attach the linker to the antibody. In some examples, PolyEthyleneGlycol (PEG), or PEG-like derivative may be added to the linker in order to improve their solubility. Linkers inherently have shorter half-lives than their antibody counterparts, and therefore typically need to be modified.

Cleavable linkers may be cleaved in the cytosol due to a more reductive environment (e.g. disulfide-based linkers), within the intracellular compartment of lysosomes thanks to a lower pH compared to the systemic blood circulation (e.g. hydrazones linkers that are linked to antibody thiol groups generated through interchain disulfide bone reduction) or by enzymatic hydrolysis, by lysosomal proteases for example, in the case of peptide linkers.

In one embodiment the agent that is coupled to the antibody of the invention is a cytotoxic agent. The cytotoxic agent may be cleavable or uncleavable. In a further embodiment, the antibody or fragment thereof as disclosed herein is coupled to an agent including, but not limited to, mertansine (Meytansinoid DM1; N2'-deactyl-N2'-(3-mercapto-1-oxopropyl)-maytansine), maytansine derivative 4 (DM4), emtansine (mertansinelinked to antibody via -4-3-mercapto-2,5-dioxo-1-pyrrolidinylmethyl)-cyclohexanecarboxylic acid linker), monomethyl auristatin E (MMAE), monomethyl auristatin F (MMAF), ricin, diphtheria toxin, doxorubicin, *Pseudomonas aeruginosa* exotoxin, antitumor agent from the calicheamicin class and pyrrolobenzodiaazepine.

In another embodiment, there is provided a nucleic acid encoding an antibody as disclosed herein wherein the heavy chain comprises the sequence as shown in SEQ ID NO: 10. In a further embodiment, there is provided a nucleic acid encoding a heavy chain variable region comprising at least one heavy chain complementarity determining region (CDR) amino acid sequence including, but not limited to SEQ ID NO: 2, SEQ ID NO: 3, and SEQ ID NO: 4.

In another embodiment, there is provided a nucleic acid encoding an antibody as disclosed herein wherein the light chain comprises the sequence as shown in SEQ ID NO: 11. In a further embodiment, there is provided a nucleic acid encoding a light chain variable region comprising at least one light chain complementarity determining region (CDR) amino acid sequence including, but not limited to SEQ ID NO: 5, SEQ ID NO: 6, and SEQ ID NO: 7. The nucleic acid may have a nucleotide sequence of SEQ ID NO: 10 or SEQ ID NO: 11.

The term "nucleic acid" used herein refers to a polymer of deoxyribonucleotides or ribonucleotides that exists in either a single-stranded or a double-stranded form. The polynucleotide includes RNA and DNA (genomic DNA and cDNA) sequences as well as analogues of natural polynucleotides unless mentioned otherwise.

The nucleic acid also includes nucleotide sequences encoding the amino acid sequences of the heavy and light chain variable regions of the antibody specifically binding to the α-chain of the c-Met protein and nucleotide sequences complementary thereto. The complementary sequences include completely complementary sequences and substantially complementary sequences that may hybridize with nucleotide sequences encoding amino acid sequences of the heavy and light chain variable regions of the antibody specifically binding to the extracellular region of the c-Met protein under stringent conditions known in the art. One way of achieving moderately stringent conditions involves the use of a prewashing solution containing 5×SSC, 0.5% SDS, 1.0 mM EDTA (pH 8.0), hybridization buffer of about 50% formamide, 6×SSC, and a hybridization temperature of about 55 degrees C. (or other similar hybridization solutions, such as one containing about 50% formamide, with a hybridization temperature of about 42 degrees C.), and washing conditions of about 60 degrees C., in 0.5×SSC, 0.1% SDS. Generally, highly stringent conditions are defined as hybridization conditions as above, but with washing at approximately 68 degrees C., 0.2×SSC, 0.1% SDS. SSPE (1×SSPE is 0.15M NaCl, 10 mM NaH.sub.2 PO.sub.4, and 1.25 mM EDTA, pH 7.4) can be substituted for SSC (1×SSC is 0.15M NaCl and 15 mM sodium citrate) in the hybridization and wash buffers; washes are performed for 15 minutes after hybridization is complete. It should be understood that the wash temperature and wash salt concentration can be adjusted as necessary to achieve a desired degree of stringency by applying the basic principles that govern hybridization reactions and duplex stability, as known to those skilled in the art.

In addition, nucleotide sequences encoding the amino acid sequences of the heavy and light chain variable regions may be mutated. The mutations include addition, deletion or substitution of nucleotides, and non-conservative or conservative substitution of amino acids. Polynucleotides encoding the amino acid sequences of the heavy and light chain variable regions of an antibody specifically binding to the α-chain of the c-Met protein are understood to include nucleotide sequences substantially identical to the nucleotide sequences described above. These substantially identical nucleotide sequences may possess at least 80% homology, at least 90% homology, or at least 95% homology to the original nucleotide sequences following maximum sequence alignment using an algorithm known in the art.

According to an embodiment of the present invention, there is provided a recombinant vector. In an embodiment, the recombinant vector comprises a polynucleotide encoding an antibody heavy chain variable region comprising at least one heavy chain complementarity determining region (CDR) amino acid sequence including, but not limited to SEQ ID NO: 2, SEQ ID NO: 3, and SEQ ID NO: 4; or a polynucleotide encoding an antibody light chain variable region comprising at least one light chain complementarity determining region (CDR) amino acid sequence including, but not limited to SEQ ID NO: 5, SEQ ID NO: 6, and SEQ ID NO: 7.

In an embodiment, the recombinant vector comprises a nucleic acid encoding a heavy chain variable region having an amino acid sequence of SEQ ID NO: 8 or a nucleic acid encoding a light chain variable region having an amino acid sequence of SEQ ID NO: 9. In some embodiments, the recombinant vector includes a nucleic acid encoding a heavy chain variable region having an amino acid sequence of SEQ ID NO: 8 and a nucleic acid encoding a light chain variable region having an amino acid sequence of SEQ ID NO: 9.

In some embodiments of the recombinant vector, the nucleic acid encoding a heavy chain variable region may have the nucleotide sequence of SEQ ID NO: 10, and the nucleic acid encoding a light chain variable region may have the nucleotide sequence of SEQ ID NO: 11.

The term "vector" used herein refers to a means, typically a nucleic acid, of transporting and expressing a target gene in a host cell. For example, the vector may include a plasmid vector, a cosmid vector, or a virus vector, such as a bacteriophage vector, an adenovirus vector, a retrovirus vector, and an adeno-associated virus vector. The recombinant vector may be prepared by manipulating a plasmid, a phage, or a virus known in the art.

In the recombinant vector, a nucleic acid encoding amino acid sequences of the heavy and light chain variable regions may be operatively linked to a promoter. The term "operatively linked" refers to a functional linkage between a transcription regulating nucleotide sequence (for example, a promoter sequence) and other nucleotide sequences. Thus, the transcription regulating nucleotide sequence may regulate transcription and/or translation of other nucleotide sequences.

The recombinant vector may be constructed for cloning or expression. For example, a recombinant expression vector may be a vector known in the art for expressing foreign proteins in plants, animals or microorganisms. The recombinant vector may be constructed using various methods known in the art.

The recombinant vector may be constructed for use in prokaryotic or eukaryotic host cells. When a prokaryotic cell is used as the host cell, the expression vector generally includes a strong promoter capable of initiating transcription, a ribosome binding site for initiating translation, and a transcription/translation termination sequence. When a eukaryotic cell is used as the host cell, the vector may contain an origin of replication. A promoter in an expression vector for a eukaryotic host cell may be derived from a mammalian cell genome or a mammalian virus. A transcription termination sequence in an expression vector for a eukaryotic host cell is, in general, a polyadenylation sequence.

A vector system capable of expressing the heavy and light chain variable regions of the antibody may involve simultaneous expression of the heavy and light chain variable regions from a single vector, or independent expression of the heavy and light chain variable regions from separate vectors. In the latter system, two vectors may be introduced into the host cell by either co-transformation or targeted transformation.

According to an embodiment of the present invention, there is provided a host cell including a polynucleotide encoding a heavy chain variable region having an amino acid sequence of SEQ ID NO: 8 and a polynucleotide encoding a light chain variable region having an amino acid sequence of SEQ ID NO: 9.

The host cell may be transformed with a recombinant vector including a polynucleotide encoding a heavy chain variable region having an amino acid sequence of SEQ ID NO: 8 and polynucleotide encoding a light chain variable region having an amino acid sequence of SEQ ID NO: 9.

The host cell, which is capable of stably and continuously cloning or expressing the recombinant vector, may be any host cell known in the art. The nucleic acid or the recombinant vector including the same may be transferred into the host cell using a method known in the art.

According to an embodiment, there is provided a pharmaceutical composition comprising antibodies, or fragments thereof specifically binding the α-chain of the c-Met protein as described herein. The pharmaceutical composition may further comprise one or more pharmaceutically acceptable excipients, or vehicles, or carriers. In other embodiments, the composition further comprises an antitumour agent, an immunostimulatory agent, an immunomodulator, a corticosteroid or a combination thereof. In one embodiment, the antitumour agent is a cytotoxic agent, an agent that acts on tumour neovasculature or a combination thereof. In another embodiment, the immunomodulator is cytokine, chemokine, adjuvant or a combination thereof. In yet another embodiment, the immunostimulatory is an interleukine-2, α-interferon, γ-interferon, tumour necrosis factor-α, immunostimulatory oligonucleotides or a combination thereof. In a further embodiment, the corticosteroid is prednisone and docetaxel.

In one embodiment, the antibodies of the present invention may be used in a method of treating/preventing cancer. The method includes administration of a pharmaceutically effective amount of an antibody, a fragment thereof, a nucleic acid or a pharmaceutical composition as described above and herein. The method of the invention may include in some embodiments administering the pharmaceutical effective amount of the antibody with one or more further therapeutic compounds, wherein administration is simultaneous, sequential or separate.

In a further embodiment, cancer to be treated or prevented by the antibody of the present invention includes, but is not limited to, breast cancer, lung cancer including, but not limited to, small-cell lung cancer and non-small-cell lung cancer, liver cancer including but not limited to hepatoma and hepatocellular adenoma, gastric cancer, squamous cell carcinoma, adenocarcinoma of the lung, squamous cell carcinoma of the lung, peritoneal carcinoma, skin cancer, melanoma in the skin or eyeball, rectal cancer, oesophagus cancer, small intestinal tumour, endocrine gland cancer, parathyroid cancer, adrenal cancer, soft-tissue sarcoma, urethral cancer, chronic or acute leukaemia, cancer, lymphocytic lymphoma, gastrointestinal cancer, pancreatic cancer, glioblastoma, cervical cancer, ovarian cancer, bladder cancer, colon cancer, large intestine cancer, endometrial carcinoma or uterine carcinoma, salivary gland tumor, kidney cancer, prostate cancer, vulvar cancer, thyroid cancer, or various types of head and neck cancers.

In a further embodiment, there is provided a method for treating or preventing cancer comprising administration of an effective amount of an antibody as disclosed herein, wherein cancer includes, but is not limited to, breast cancer, lung cancer, liver cancer, gastric cancer, brain cancer, blood cancer, colon cancer, pancreatic cancer and prostate cancer. In a further embodiment, there is provided an antibody as disclosed herein, in the manufacture of a medicament for treating and/or preventing cancer. In some embodiments, the cancer to be treated of prevented may be any form of cancer. Any form of tumour or cancer may be used in the invention including for example, a benign tumour and a metastatic malignant tumour. Examples of cancers include, but are not limited to, brain cancer such as glioblastoma and neuroblastoma, blood such as lymphoma and leukaemia, colon cancer, pancreatic cancer, prostate cancer, gastric cancer, lung cancer, breast cancer, bladder cancer, melanoma, head and neck cancer, oesophagus cancer and cervix cancer. Other examples of tumours include, but are not limited to, haematological malignancies and solid tumours. Solid tumours include for instance a sarcoma arising from connective supporting tissues, a carcinoma arising from the body's glandular cells and epithelial cells or a lymphoma, a cancer of lymphatic tissue, such as the lymph nodes, spleen and thymus.

In one embodiment, there is a provided a method of diagnosing cancer comprising detection of aberrant expression of c-Met by administering an antibody as disclosed herein, for detecting c-Met. The term "aberrant expression" as used herein relates to the expression of c-Met protein, c-Met cDNA and/or RNA that differs significantly from the expression of c-Met protein, c-Met cDNA and/or RNA that is found in a healthy tissue or in a healthy individual that does not have or is not at risk of having a disease including cancer. In a further embodiment, there is provided the use of an antibody as disclosed herein for detecting cells with aberrant c-Met expression. In yet another embodiment there is provided the use of an antibody, as disclosed herein, as a cancer prognosis marker.

In some embodiments, the pharmaceutical composition as described above and herein may further comprise a therapeutic compound (or an agent or a molecule or a composition). A "therapeutic" compound as defined herein is a compound (or an agent or a molecule or a composition) capable of acting prophylactically to prevent the development of a weakened and/or unhealthy state; and/or providing a subject with a sufficient amount of the complex or pharmaceutical composition or medicament thereof so as to alleviate or eliminate a disease state and/or the symptoms of a disease state, and a weakened and/or unhealthy state. In one example, the therapeutic compound includes but is not limited to an apoptosis promoting compound, a chemotherapeutic compound or a compound capable of alleviating or eliminating cancer in a patient. Examples of apoptosis promoting compounds include but are not limited to Cyclin-dependent Kinase (CDK) inhibitors, Receptor Tyrosine Kinase (RTK) inhibitors, BCL (B-cell lymphoma) family BH3 (Bcl-2 homology domain 3)-mimetic inhibitors and Ataxia Telangiectasia Mutated (ATM) inhibitors.

The term "treat" or "treating" as used herein is intended to refer to providing an pharmaceutically effective amount of a peptide of the present invention or a respective pharmaceutical composition or medicament thereof, sufficient to act prophylactically to prevent the development of a weakened and/or unhealthy state; and/or providing a subject with a sufficient amount of the complex or pharmaceutical composition or medicament thereof so as to alleviate or eliminate a disease state and/or the symptoms of a disease state, and a weakened and/or unhealthy state.

In some embodiments, there is provided the use of an antibody, as described herein, for protein purification, or for neutralizing, disrupting, modifying, antagonizing or for inhibiting protein-protein interactions, for example c-Met-HGF interaction, thereby affecting the c-Met-HGF axis.

Specific Illustrative Embodiments

Development and Initial Characterisation of Anti-α-Chain c-Met Antibodies

The α-chain of human c-Met was prokaryotically expressed and purified. Purified α-chain was used to immunise BALB/c mice. To obtain hybridoma cells producing anti-α-chain c-Met antibodies, the spleen cells of immunised mice were fused with SP2/0-Ag14 cells. Hybridoma cells were single-cell cloned and cell supernatant from monoclonal hybridoma clones were screened for anti-α-chain c-Met reactivity mainly by Western blotting and cell staining. Post primary and secondary antibody screening (FIG. 1 D), a panel of 21 antibodies were selected for isotype characterisation and epitope mapping. Antibody isotyping was performed by dipping commercially-available isotyping strips into monoclonal hybridoma supernatant. All 21 monoclonal antibodies share the same IgG isotype (but not the same subclass) and kappa light chain (Table 2).

Identifying the region of c-Met bound by the antibody is important in determining whether the antibody might be able to block c-Met from binding to its ligand, HGF. Using an ELISA-based assay (Pepscan), synthesised peptides were added to strepatvidin-coated plates and antibody binding to their respective epitopes was determined colorimetrically. The peptides were consecutive overlapping peptides that span the entire c-Met α-chain. In total, 10 different antibody binding regions from the α-chain were identified from the 21 monoclonal cell supernatants tested, indicating that there is no one main region that is highly

TABLE 1

Epitope mapping and isotyping of anti-α-chain c-Met monoclonal antibodies.

| Binding region | Monoclonal antibody | IgG subclass | Light chain |
|---|---|---|---|
| 1 | 16 | IgG2A | Kappa |
| 2 | 12 | IgG1 | Kappa |
|   | 20 |       |       |
| 3 | 11 | IgG1 | Kappa |
|   | 21 |       |       |
| 4 | 14 | IgG1 | Kappa |
|   | 18 |       |       |
|   | 17 |       |       |
|   | 19 | IgG2B |     |
| 5 | 3  | IgG1 | Kappa |
|   | 5  |       |       |
| 6 | 4  | IgG2A | Kappa |
| 7 | 1  | IgG1 | Kappa |
|   | 2  |       |       |
|   | 9  |       |       |
| 8 | 6  | IgG1 | Kappa |
|   | 10 |       |       |
|   | 13 |       |       |
|   | 17 |       |       |
| 9 | 8  | IgG1 | Kappa |
| 10 | 7 | IgG1 | Kappa |
|   | 15 |       |       | immunogenic. A simplified diagram of the antibody binding regions on c-Met α-chain is shown in FIG. 1A. The antibody binding regions were also mapped onto the crystal structure of c-Met, PDB accession number 1SHY (FIGS. 1B & C). The results of initial antibody characterisation are summarised in Table 2.

Further Characterisation of Purified Anti-α-Chain c-Met Monoclonal Antibodies

From the panel of 21 monoclonal antibodies, 11 antibodies were selected for ascites production and purification. Purified antibodies were further characterised by Western blotting, immunoprecipitation, flow cytometry, and agonist/antagonist activity by cell scattering.

Anti-α-chain c-Met monoclonal antibodies were purified from mouse ascites using protein A beads. Purified antibody was resolved on a SDS-PAGE gel and stained with Coomassie blue dye (data not shown). Other than the expected two bands corresponding to the heavy (~51 kD) and light (~25 kD) chain of an antibody, no other protein bands were observed in the Coomassie-stained gel, suggesting that the purification of monoclonal antibodies from mouse ascites was successful.

Figure 2:
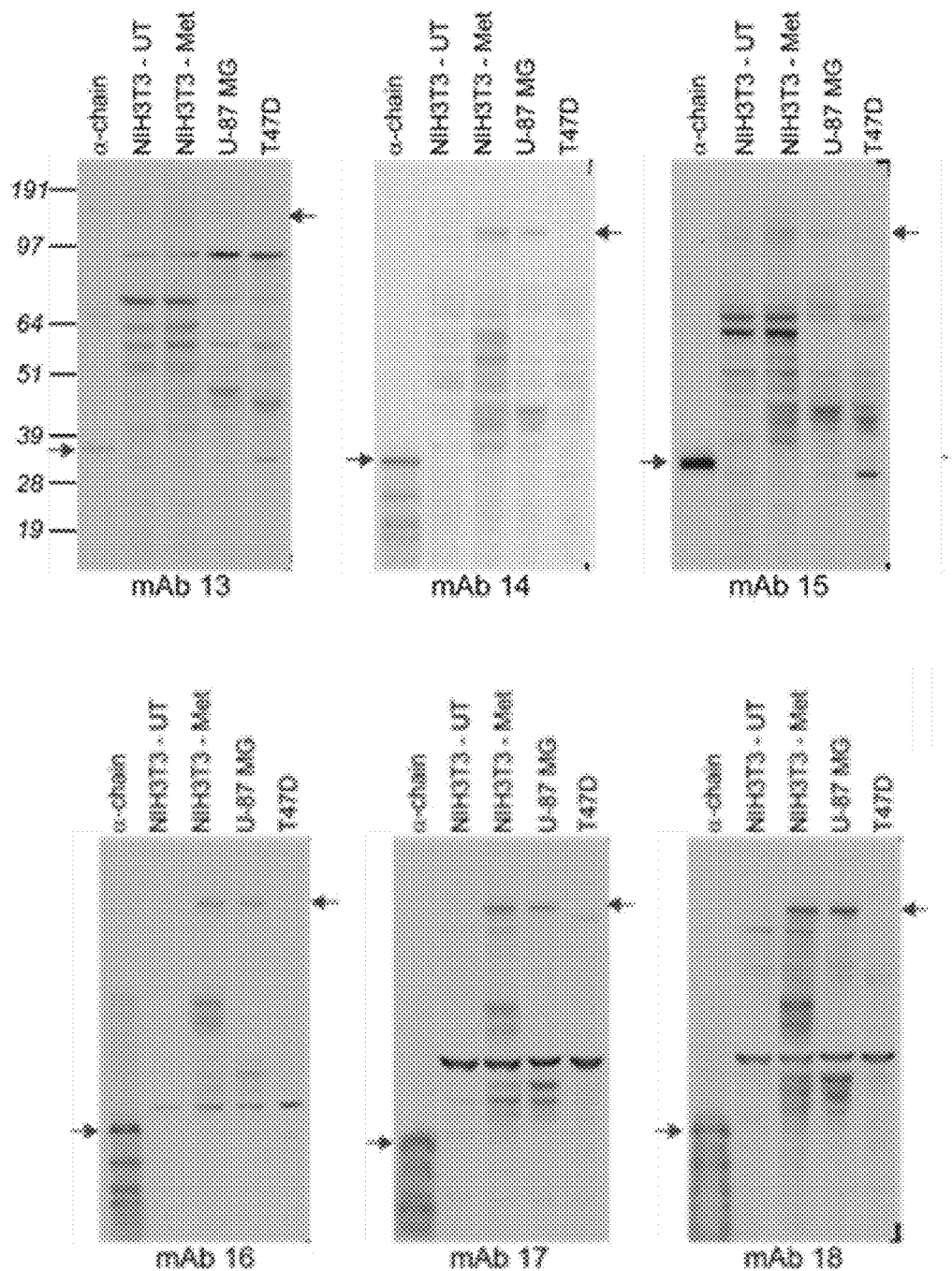
FIG. 2 presents photographic images of Western Blots using purified anti-α-chain c-Met monoclonal antibodies, Eleven hybridoma clones (mAb2, mAb4, mAb8, and mAb11-18) were selected for ascites production. Monoclonal antibodies were purified from ascites and tested again for reactivity against full length c-Met in whole cell lysates. 50 μg of whole cell lysate was obtained from untransfected NIH3T3 cells (UT), NIH3T3 cells transfected with full length human c-Met (Met), U-87 MG cell lines and T47D cell lines. U-87MG cells and T47D cells express high level and non-detectable levels of c-Met respectively. Monoclonal antibodies are used at concentration of 1 μg/mL. 10 ng of purified α-chain was used as positive control. AF276 antibody was used as control. Upper and middle arrows indicate c-Met precursor (170 kD). Bottom arrows indicate purified α-chain. Molecular weights are noted aside, in kilodaltons.

To ensure that the monoclonal antibodies retained their anti-α-chain activity after ascites production and purification, purified monoclonal antibodies were characterised by Western blotting (FIG. 2). 1 µg/mL of purified monoclonal antibodies was used to detect purified c-Met α-chain, c-Met expressed after transfection of NIH3T3 cells and endogenous c-Met in U-87MG cells. All monoclonal antibodies, except mAb 13 and 15, successfully detected purified c-Met α-chain, transfected and endogenous human c-Met. mAb 13 and 15 had low specificity towards c-Met. mAb 2 and 14 were observed to have higher affinity towards c-Met, compared to mAb 13 and 15. mAb 4, 8, 16, 17 and 18 have higher affinity towards c-Met and fewer non-specific bands compared to mAb 2, 13, 14 and 15. Despite recognising different epitopes (FIG. 1A), most of the anti-α-chain c-Met monoclonal antibodies share the same pattern of band recognition with mAb 11 and 12. This suggests that the band profiles of mAb 11 and 12 are completely specific. mAb 11 and 12 are thus the best monoclonal antibodies to use on Western blots as they detected c-Met with good affinity and specificity. Horseradish peroxidase (HRP) was conjugated to mAb 12 (mAb 12-HRP) and used as a tool in this study for detecting precursor c-Met and mature c-Met α-chain.

Figure 3:
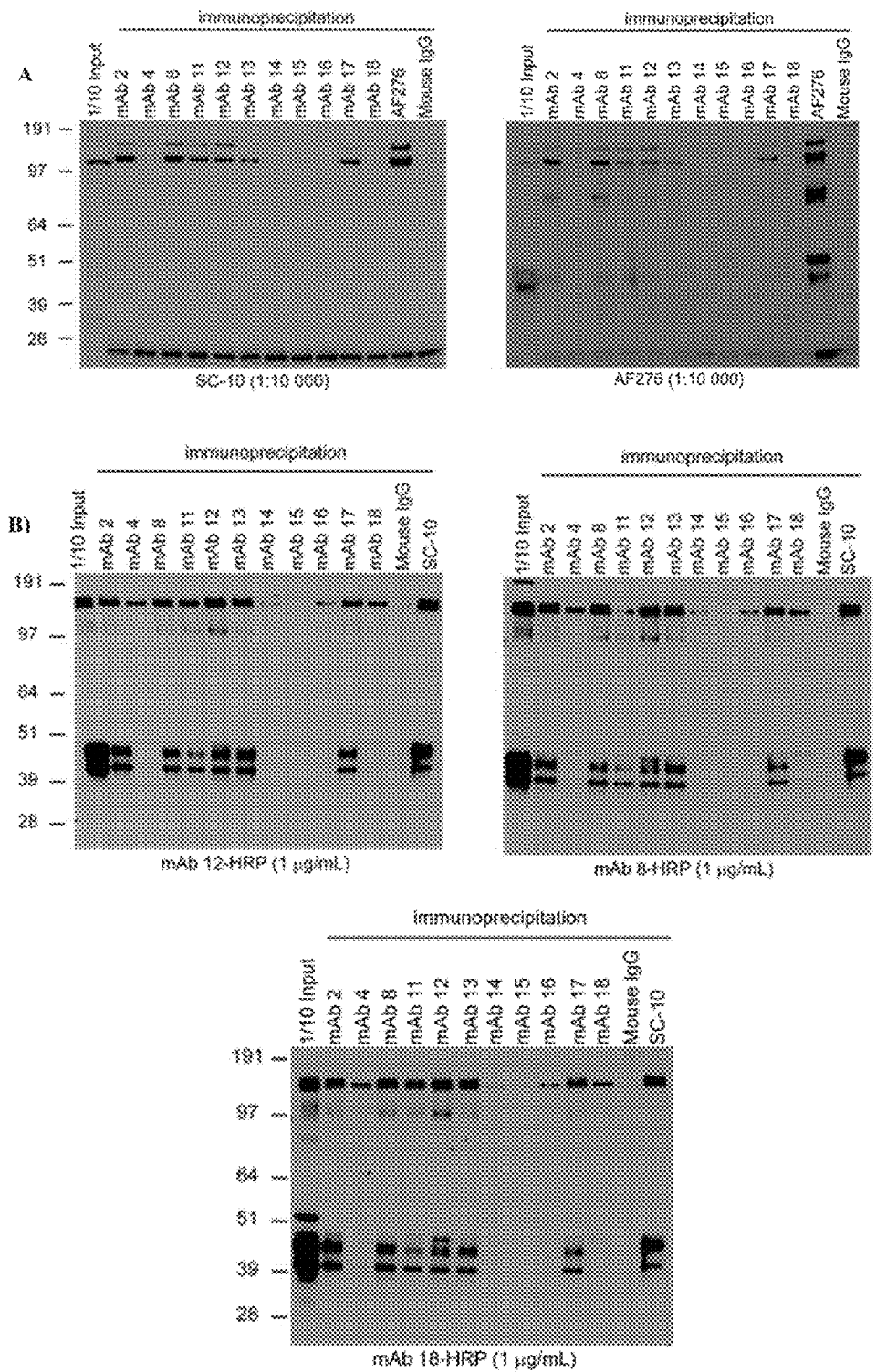
FIG. 3 depicts images of Western-blottings showing that anti-α-chain c-Met monoclonal antibodies immunoprecipitate endogenous c-Met. Monoclonal antibodies were produced from ascites and purified using protein A beads. Purified antibodies were tested for their ability to immunoprecipitate endogenous c-Met from SNU-5 cell lysate. 1 μg/mL antibodies were used for immunoprecipitation. Commercial anti-Met antibodies, SC-10 and AF276, and mouse IgG were used as controls Immunoprecipitated SNU-5 cell lysate was analysed by Western blotting using A) SC-10 and AF276 antibody, and B) HRP-conjugated monoclonal antibodies developed from this screen. mAb 8, 12 and 18 were previously shown to recognise different epitope and work well on Western blots. Molecular weights are noted aside, in kilodaltons.

To further characterise the monoclonal antibodies reactivity against c-Met α-chain, the antibodies were used to immunoprecipitate endogenous c-Met from SNU-5 cell lysate. SNU-5 is a human gastric cell line that expresses high levels of c-Met. Immunoprecipitated cell lysates were analysed by Western blotting (FIG. 3) using the commercial SC-10 and AF276 antibody. Although SC-10 and AF276 antibodies are raised against different regions of c-Met, both SC-10 and AF276 share similar Western blot band profiles. Most of our monoclonal antibodies successfully immunoprecipitated the 170 kD precursor c-Met (α- and β-chain linked together). Interestingly, a 145 kD protein band, which corresponds to the mature c-Met β-chain, was also observed on the Western blot, suggesting that the c-Met β-chain was pulled down together with its α-chain. In order to ensure that mature α-chain was immunoprecipitated, mAb 12-HRP (developed from this screen) was used to analyse the same immunoprecipitated SNU-5 cell lysate on Western blots. mAb 8 and 18, which was also developed in this screen, were conjugated to HRP and also used to detect c-Met α-chain. mAb 8, 12 and 18 recognise different epitopes on c-Met (FIG. 1A) but all HRP-conjugated antibodies successfully detected mature c-Met α-chain and precursor c-Met strongly.

Flow cytometry was used to determine if our monoclonal antibodies could bind to native c-Met on live cells. SNU-5 cells were incubated with 1 µg/mL of monoclonal antibody. Binding of anti-α-chain c-Met monoclonal antibodies to native c-Met expressed on the cell surface of SNU-5 cells was detected using anti-mouse secondary antibody conjugated with FITC dye. T47D, a human breast cancer cell line expressing low levels of c-Met, was used in this assay to determine if the antibodies bind non-specifically to the cell surface. The flow cytometry results of purified monoclonal antibody treated-T47D cells were indistinguishable from the negative control (secondary antibody only), indicating that monoclonal antibodies do not bind non-specifically to the cell surface (data not shown). Flow cytometry results obtained with SNU-5 cells showed that the antibodies fell into three distinct groups with different fluorescence intensity towards native c-Met: strong fluorescence intensity, intermediate fluorescence intensity and weak fluorescence intensity (FIG. 4). mAb 2 and 13 showed the strongest fluorescence intensity in this assay. mAb 8, 11, 12 and 17 showed intermediate fluorescence intensity while mAb 4, 14, 15, 16 and 18 showed weak fluorescence intensity (as demonstrated by the small peak shift).

Figure 5:
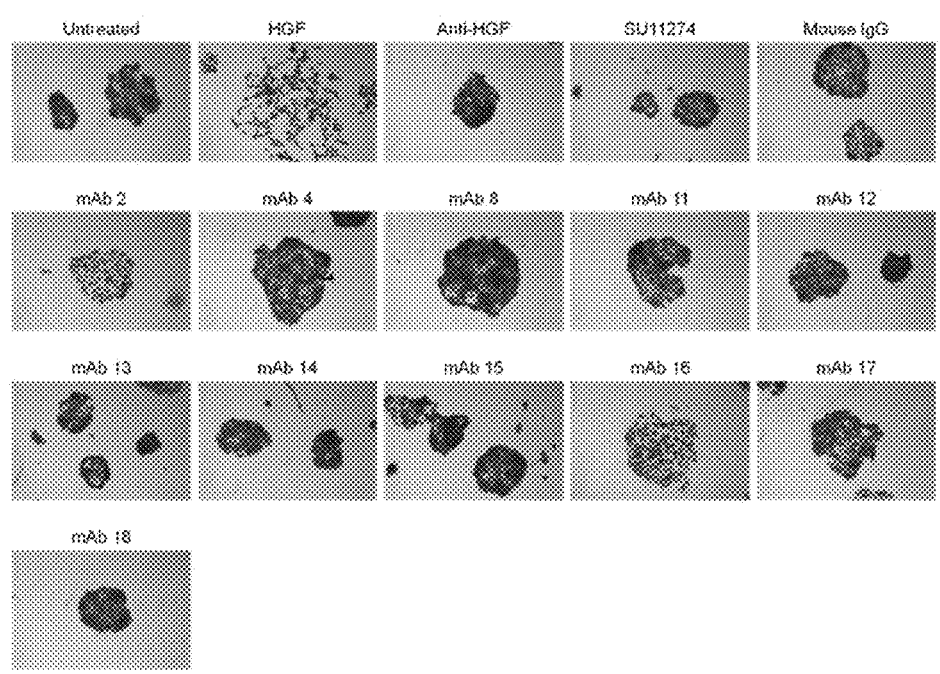
FIG. 5 presents images of HaCaT cells demonstrating the effects of purified anti-α-chain c-Met monoclonal antibodies on cell scatter. HaCaT cells were serum-starved for 24 hrs before treatment. Monoclonal antibodies (1 μg/mL) and HGF 24 hrs before fixation. Cells were then stained with crystal violet for visualisation. Anti-HGF antibody (anti-HGF), commercially-obtained mouse immunoglobulin G (IgG), and c-Met small molecule inhibitor SU11274 were used as controls. UT: Untreated.

Cell scattering is one of the biological hallmarks of c-Met activation. Agonist bivalent monoclonal antibodies targeting c-Met would activate c-Met and cause cells to become motile and disperse. Here, we examine the effects of purified anti-α-chain c-Met monoclonal antibodies on cell scatter. HaCaT cells were seeded at low density and allowed to grow until colonies formed. Cells were serum-starved for 24 hrs before incubating with 1 µg/mL monoclonal antibodies for 24 hrs. Cells were then fixed and stained with crystal violet. As a control, cell scatter of HaCaT cells was induced with 10 ng/mL of HGF (FIG. 5). Presence of non-specific IgG (mouse IgG) did not affect scattering. Anti-HGF antibody and SU11274 were used as controls. SU11274 is a small molecule inhibitor of c-Met. Anti-HGF and SU11274-treated cell colonies remained circular. No cell scatter was observed in cells treated with monoclonal antibodies alone (FIG. 5). This suggests that the monoclonal antibodies are not agonist towards c-Met activated cell scatter.

mAb2 and 13 Reduce Cell Growth in SNU-5 Cells mAb 2 and 13 showed the strongest binding to native c-Met in flow cytometry. In order to determine if these antibodies have any physiological effects on tumour cells, 10 µg/mL of mAb was added to SNU-5 cells. The effects of mAb 2 and 13 on SNU-5 cell viability and caspase activation were recorded after 72 hrs of antibody treatment (FIG. 7A). mAb 11 and 18, which demonstrated intermediate and weak affinity in flow cytometry respectively, were used as controls. SU11274 showed a significant reduction in cell viability and high caspase activation. This indicates SU11274 mode of mechanism is by activation of caspase which in turn result in apoptosis of SNU-5 tumour cells. In contrasts, cells treated with mAb 2 or 13 have reduced cell viability, and also reduced caspase activation. To determine the effects the anti-α-chain monoclonal antibody on cell growth, a cell count was performed 72 hours post antibody treatment. mAb 2 showed the strongest cell growth reduction followed by mAb 13. mAb 18 had slightly reduced cell growth and mAb 11 had no effect (FIG. 7A).

To further demonstrate the effects of anti-α-chain monoclonal antibody on cell growth, SNU-5 cells were prestained with the CellTracker green BODIPY dye before antibody treatment. CellTracker BODIPY dye is a membrane permeable dye that enters cells freely. Once in the cell, the dye is converted to a membrane impermeable product which labels the cell green. The dye is passed on to dividing daughter cells but is not transferable to neighbouring cells. Dividing cells would fail to retain the green dye as it is being diluted to progeny cells. Cells were treated with 10 µg/mL of monoclonal antibodies for 6 days and dye retention in cells was analysed by flow cytometry. As expected, the levels of fluorescence intensity in untreated cells, mAb 11 and mAb 18-treated cells fell to levels similar to unstained cells (FIGS. 7B & C). mAb 2 and 13 retained significant levels of green fluorescence indicating cell growth reduction.

Internalisation of mAb 2 and 13 in SNU-5 Cells

Figure 8:
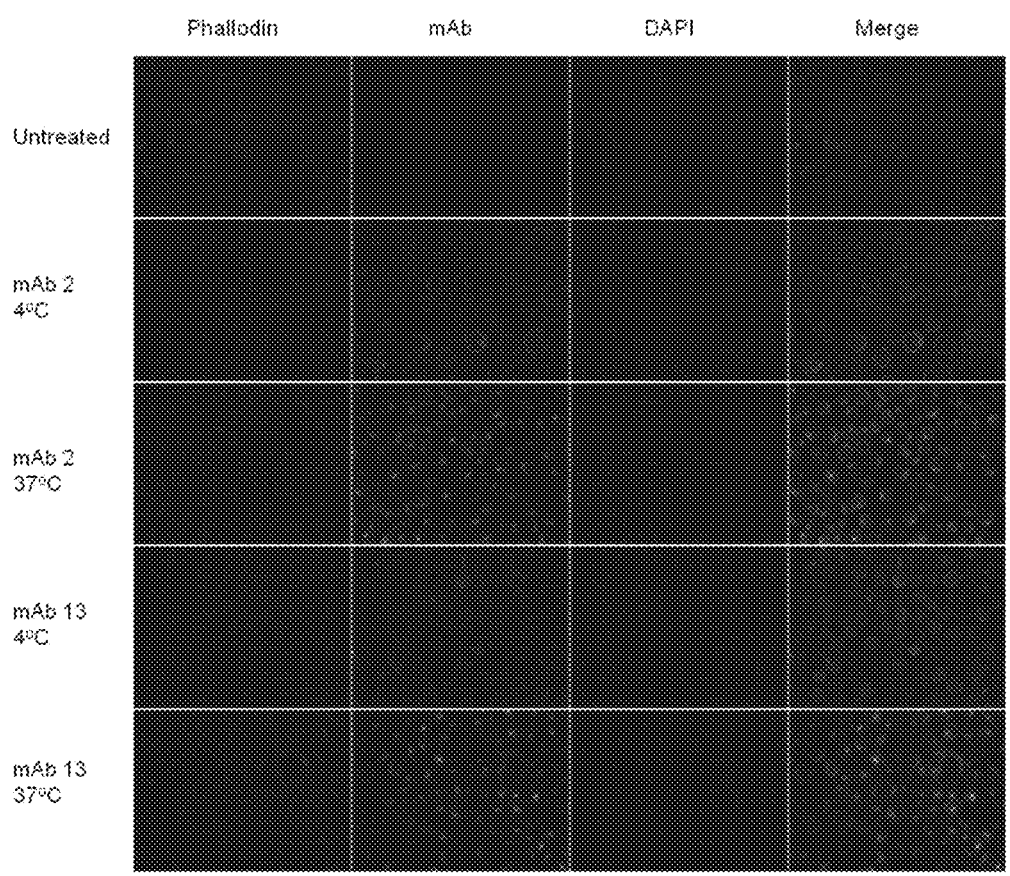
FIG. 8 presents photographic images showing the intracellular immunofluorescence staining of mAb 2 and 13 in SNU-5 cells. Live SNU-5 cells are incubated with 10 µg/mL of monoclonal antibody for an hour at the indicated temperatures. Cells were harvested and spun onto microscope slides. Cells were fixed in 4% PFA (paraformaldehyde)/PBS (phosphate buffered saline) and permeabilised. mAb 2 and 13 were detected using anti-mouse Alexa Fluor®488-conjugated secondary antibody. Phalloidin and DAPI, which stained F-actin and nucleus respectively, were used as counter stain.

In order to determine if mAb 2 and 13 were internalised into the cell upon antibody binding, SNU-5 cells were incubated with 10 µg/mL of anti-α-chain monoclonal antibody. Monoclonal antibody treated cells were fixed and permeablised. Bound and internalised antibody was detected by anti-mouse Alexa Fluor®488-conjugated secondary antibody. Antibody localisation was observed by confocal microscopy. At 4° C., staining of both mAb 2 and 13 were observed to localised on the cell membrane with diffused cytoplasmic staining (FIG. 8). Antibody localisation on the cell surface became less prominent at 37° C. while increase staining was observed in the cytoplasm. Cytoplasmic staining was observed to accumulate in the cell, suggesting that mAb 2 and 13 were internalised upon binding to c-Met and accumulate within the cell.

Temperature Sensitivity of mAb 2

Figure 9:
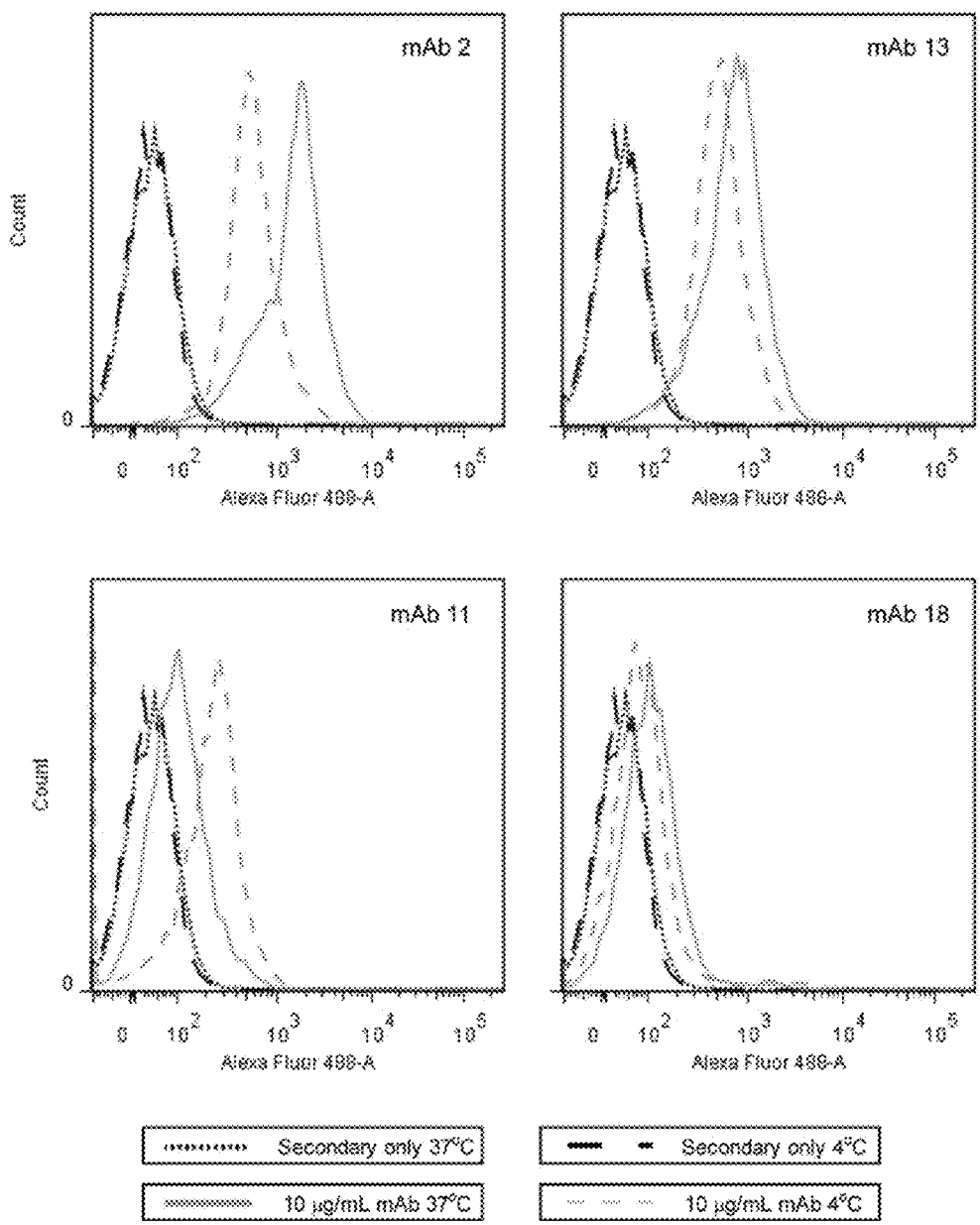
FIG. 9 is a series of histogram plots representative of flow cytometry analysis of anti-α-chain c-Met monoclonal antibody binding to live SNU-5 cells at different temperatures. Live SNU-5 cells were treated with respective monoclonal antibody for 1 hr at 4° C. or 37° C. Cells were harvested. Anti-α-chain c-Met monoclonal antibody binding was determined by Alexa Fluor®488-conjugated anti-mouse secondary antibodies and cells were analysed by flow cytometry.

To determine if temperature affects the binding affinity of anti-α-chain monoclonal antibody to native c-Met, mAb 2, 13, 11 and 18 were incubated with live SNU-5 cells at 4° C. or 37° C. Binding of monoclonal antibody to native c-Met expressed on the cell surface of live SNU-5 cells was detected using anti-mouse secondary antibody conjugated with Alexa Fluor®488 dye and analysed by flow cytometry. Antibody binding, which correlates with fluorescence intensity, was compared at the different temperatures. Interestingly, each antibody demonstrated a peak shift between different temperatures (FIG. 9), indicating a decrease in antibody binding at 4° C. Among the four antibodies tested, mAb 2 showed the most drastic peak shift. It is plausible that the reduction of antibody binding is due to the unavailability of antibody's epitope on native c-Met expressed on live SNU-5 cells. c-Met is a dynamic protein at normal physiological temperature and becomes rigid at low temperature, causing certain epitopes to be obscured.

Detailed Mapping of mAb 2 Epitope

Previous pepscan analysis was designed to narrow down an antibody's epitope to be within a maximum of 15 amino acid residues which, not all residues may be involved in antibody-Met interaction. To further understand the decrease in antibody binding at low temperature, the epitope of mAb 2 was mapped to greater detail. Pepscan analysis of mAb 2 demonstrated that mAb 2 bound to peptides O28 and O29 with equal affinity. This indicates that the epitope of mAb 2 is shared by both peptides. To identify residues critical for mAb 2 interaction, variations of peptides O28 and O29, where each amino acid residue is substituted for an alanine residue, were synthesised. Utilising the same ELISA-based assay used previously, purified mAb 2 was added to each alanine-substituted peptide. Loss of antibody interaction to a peptide would demonstrate the importance of the substituted amino acid residue in mAb 2-Met interaction.

Figure 10:
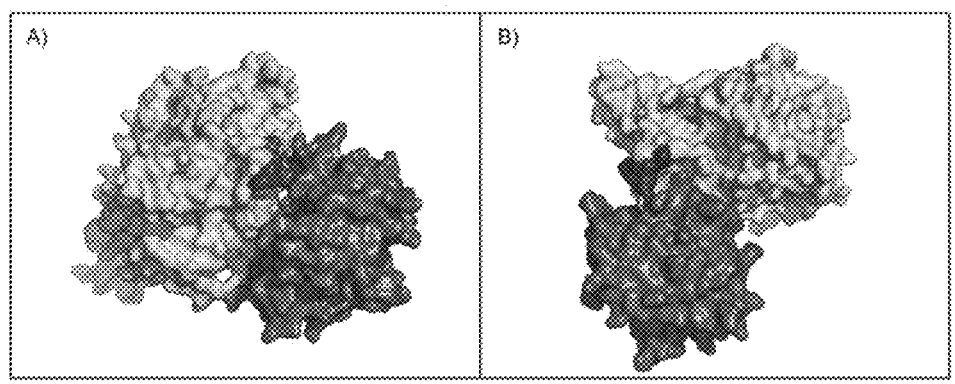
FIG. 10 is a representative pairs of snapshots from the computer simulation of c-Met in complex with HGF showing the identification of residues critical for mAb 2 epitope. Alanine scan of mAb 2 epitope identified several non-consecutive residues important for mAb 2-Met interaction. Mapping of the critical residues on c-Pvlet crystal structure (PDB accession number 1SHY) grouped the residues into two clusters i.e. residues that lie on c-Met surface (in black) and buried within c-Met (in mid-grey). c-Met is highlighted in light grey and HGF in dark grey. Again, the protein complex is shown from two different viewpoints (A) and (B).

Comprehensive mapping of mAb 2 epitope revealed that the residues critical for mAb 2-Met interaction are not consecutive residues. This is in line with the observed character of mAb 2 i.e. mAb 2 have high affinity towards native c-Met and not to denatured c-Met. Only when a protein is in its tertiary conformation that non-consecutive resides lie side by side and come together to form a site for protein-protein interaction. Mapping of the critical residues onto the crystal structure of c-Met (PBD accession number 1 SHY), revealed that the residues fell into two clusters (FIG. 10). One cluster, in pink, is exposed on the surface of c-Met while the second cluster (in cyan) is buried within c-Met.

c-Met is a tyrosine kinase receptor involved in a wide range of biological activities such as cell proliferation, cell motility angiogenesis and morphogenesis. Aberrant expression of c-Met correlates with tumour aggression and cancer progression. Expression of c-Met is also known to cause drug resistance towards HER2, EGFR and B-RAF treatment. c-Met is thus an attractive target for cancer therapy.

The inventors have developed a panel of murine monoclonal antibodies against the α-chain of human c-Met. The inventors characterised the antibodies by Western blotting, immunoprecipitation, flow cytometry, epitope mapping and agonist/antagonist activity towards c-Met. The α-chain was used as immunogen as it was best expressed and most immunogenic among other c-Met fragments (full length n-chain, extracellular β-chain, extracellular domain of c-Met). Comparison with the commercial antibodies (SC-10 and AF276) has revealed the superior performance of the antibodies of the invention in immunoblotting. mAb 11 and 12 were the best antibodies for Western blotting as they demonstrated good affinity and specificity towards c-Met. In addition, the antibodies as disclosed herein are able to function in immunoprecipitation and ELISA. Antibodies that have higher affinity and specificity compared to the currently available commercial antibodies, and characterised in various biochemical techniques, will be valuable tools for c-Met further studies. Finally the reliability of commercial c-Met antibodies has been questioned as cancer prognosis markers. Of the five commercial c-Met antibodies examined to quantify c-Met protein levels, some antibodies had batch variation while others had non-reproducible results. This emphasises the need to develop and characterise reliable c-Met antibodies.

Despite the use of prokaryotic-expressed denatured protein as immunogen, it was still possible to obtain antibodies that recognise native c-Met protein. mAb 13, which showed poor affinity and poor specificity to c-Met by Western blotting, was, along with mAb 2, produced the highest fluorescence staining determined by flow cytometry. Clearly, mAb 2 and 13 epitopes lies in c-Met native conformation. In SNU-5 cells, mAb 2 and 13 do not activate caspase activation and do not cause cell death as suggested by lack of annexin V staining. Western blot analysis of antibody-treated cells using the senescence marker and autophagy marker, p16 and LC-3 respectively, were negative for such events (data not shown). Through the binding of mAb 2 or 13 to c-Met, the only functional effect these antibodies elicit is the reduction of SNU-5 cell growth. However, incorporation of BrdU during DNA synthesis showed no significant difference between antibody-treated and untreated cells. Finally, the antibodies of the invention are non-agonistic towards c-Met in cell scatter.

Given the advances in antibody engineering, there are several ways antibodies may be engineered for cancer therapy and diagnosis. mAb 2 and 13 bind to endogenous c-Met on live SNU-5 cells with high affinity and specificity. Immunofluorescence staining demonstrates that mAb 2 and 13, most likely mediated via endocytosis, is internalised into the tumour cell. Combining the technology in molecular imaging and nanotechnology, c-Met antibodies may be engineered into powerful tools for in vivo tumour imaging. This will provide valuable information on tumour physiology which will help improve cancer diagnosis, prognosis and therapy. c-Met antibodies may also be engineered to carry toxic payloads into tumour cells and cause tumour cell killing.

The inventors have shown treatment of SNU-5 cells with 10 μg/mL of anti-α-chain c-Met monoclonal antibody. It is also plausible as well known in the art, to use higher concentrations of antibody treatment. Testing the antibodies as disclosed herein at higher concentration might provide better insights into our antibodies' mode of action.

Partial inhibition of c-Met-induced biological activities using monoclonal anti-Met antibodies has been described in the art. The anti-Met antibody, DN-30, inhibits other c-Met-induce biological activities, but not cell motility. Another monoclonal antibody (DO-24) developed from the same immunisation as DN-30, was a full agonist capable of eliciting full c-Met activity. It has been demonstrated that more than three monoclonal antibodies are required to completely inhibit c-Met binding. The molecular mechanisms of c-Met activation by HGF are still unclear. This interaction is more complex than previously thought and from these antibody studies, it is obvious that there are critical interaction sites that are responsible for eliciting various c-Met activities. In addition, the revelation of mAb 2 cryptic epitope suggests that c-Met is a dynamic protein and this further illustrates the lack of understanding we have on c-Met physiology. mAb 2 would probably be similar to the EGFR 806 antibody, that recognizes a cryptic epitope that is only expressed on tumour cells.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples.

Materials and Methods

Cell Lines and Reagents

All cells were maintained at 37° C. in 5% $CO_2$ humidified incubator. HaCaT, U-87MG and murine NIH3T3 cells, cultured in Dulbecco's Modified Essential Medium (DMEM) high glucose with sodium pyruvate, were generous gifts from Birgit Lane (Institute of Medical Biology (IMB), Singapore), Nick Leslie (Division of Cell Signalling and Immunology, University of Dundee) and Axel Ullrich (Institute of Medical Biology (IMB), Singapore) laboratories respectively. SNU-5 cells were purchased from Korean Cell Line Bank. T47D and SNU-5 cells were cultured in RPMI 1640 media. DMEM and RPMI were obtained from Invitrogen (U.S.A.). All tissue culture medium was supplemented with 10% heat-inactivated fetal calf serum obtained from HyClone Laboratories/Thermo Scientific (U.S.A.).

Recombinant human HGF (#294-HG) and anti-human HGF (#MAB294) were purchased from R&D Systems (U.S.A.). SU11274, the c-Met small molecule inhibitor, was purchased from Calbiochem/Merck (Germany, #448101). CellTracker Green BODIPY dye (Invitrogen #C2102) was resuspended in DMSO, according to manufacturer's protocol.

Cell Harvest and Cell Lysis

Cell culture plates/dishes were rinsed with cold PBS before the cells were scraped off. Cells were collected by centrifugation. PBS was removed before quick freezing the cell pellet on dry ice. The frozen cell pellet was lysed on ice using NP40 lysis buffer (1% NP40, 150 mM NaCl, 50 mM Tris-HCL pH 8.0) containing complete protease inhibitor (Roche, United Kingdom, #11 697 498 001). Cell lysate was centrifuged at 10,000×g and the supernatant was recovered for analysis. Protein quantification was performed using a BCA kit (Pierce/Thermo Scientific), according to the manufacturer's protocol Cloning, Prokaryotic Expression and Purification of c-Met α-Chain c-Met α-chain was first cloned from the entry vector, containing full length human c-Met cDNA (Invitrogen #I0H36570), into pCR2.1 vector (Invitrogen) using the TOPO TA cloning kit (Invitrogen). Amplification of c-Met α-chain was performed using c-Met α-chain primers (alphaF: 5'-GGAATTCCATATGGAGTGTAAAGAG-GCACTAGC-3'; SEQ ID NO: 24) and alphaR: 5'-GCG-GATCCCTATCTCTTTTTTCTCTTTTCTGTGAG-3'; SEQ ID NO: 25). All plasmid extraction, gel extraction and PCR product purification protocols were performed using Qiagen (United Kingdom) kits, according to manufacturer's protocol.

For prokaryotic expression, c-Met α-chain was subcloned from pCR2.1 vector into pET19b vector (Novagen/Merck) and transformed into BL21 pLysS cells (Invitrogen). Transformed cells were grown until an OD600 0.4 to 0.6 was reached. Protein expression was induced by adding IPTG (isopropyl-β-D-thio-galactoside) to a final concentration of 1 mM. Cultures were allowed to grow for 3 hrs. Cells were recovered by centrifugation and resuspended in lysis buffer (0.3 M KCL, 50 mM KH2PO4, pH 8.0). Cell lysate was centrifuged at 33,000×g. The cell pellet obtained was resuspended in lysis buffer containing 6 M urea and incubated overnight with gentle stirring. The resulting suspension was centrifuged and the supernatant obtained was used for protein purification.

Prokaryotically expressed c-Met α-chain was affinity purified on a 1 mL IMAC (immunobilised metal affinity chromatography) Bio-Scale Mini Cartridge (Bio-Rad, U.S.A.), using the automated Profinia protein purification system (Bio-Rad). c-Met α-chain was eluted and used to immunise mice for antibody production.

Mouse Immunisation and Hybridoma Fusion

Antibody production was performed by Dr. Borek Vojtesek from Moravian Biotechnology (Czech Republic). Briefly, mice were immunised with purified human c-Met α-chain expressed from bacteria. Each injection contained 40 μg of purified c-Met α-chain. Mouse tail bleeds were taken to test for immunological response against c-Met α-chain. Two mice that gave the highest immune response against c-Met α-chain were sacrificed for hybridoma cell fusion. Spleen cells from mice were fused with SP2/0-Ag14 cells which are mouse immortal myeloma cells. Hybridoma cells were grown in selection media containing hypoxanthine, aminopterin and thymidine. Only hybridoma cells which have been successfully fused between a spleen cell and an immortal cell will survive and grow in the selection media.

Antibody Screening.

Antibody screening was performed in collaboration with Moravian Biotechnology. An outline of monoclonal antibody screening is shown in FIG. 1bis. Hybridoma cells were screened for anti-α-chain antibody production ten days after cell fusion.

Isotyping

Mouse monoclonal antibodies isotype were characterised using the commercially-available IsoQuick™ strips (Sigma-Aldrich). Isotyping strips were incubated in hybridoma cell supernatant for 5 mins. A red test line will develop on the strip. The position of the red test line is dependent on the antibody's isotype, thus by referencing to the manufacturer's isotyping chart, the antibody's isotype is determined.

Pepscan and Alanine Scan

Peptides that were linked to biotin by an SGSG linker sequence at the N-terminus were synthesised by Mimotopes (Australia). Peptides for Pepscan: Peptides that span the entire α-chain of c-Met were synthesised. A total of fifty-five peptides with consecutive, overlapping sequences were synthesised. Each peptide overlapped the previous peptide by 10 amino acid residues.

Peptides for Alanine Scan

Pepscan results showed that mAb 2 bound to peptides O28 and O29. Variations of peptides O28 and O29, where each amino acid residue was sequentially substituted for an alanine residue, were synthesised. Streptavidin-coated plates (Pierce/Thermo Scientific, #15520) were blocked with 3% BSA/PBS at room temperature. The peptides were dissolved in DMSO and stored according to manufacturer's recommendation. Streptavidin-coated plates were coated with each peptide (5 μg/mL) overnight at room temperature. Wells were washed before hybridoma supernatant or purified monoclonal antibody was added to the each well. HRP-conjugated anti-mouse antibody was added to detect bound monoclonal antibodies. ELISA substrate (Bio-Rad #172-1067) solution was prepared freshly according to the manufacturer's instructions and added to the wells. Colour change was monitored by eye and the reaction was stopped by adding 100 mM sulphuric acid. Absorbance was read at 450 nM in a microplate reader (SPECTRAmax PLUS$^{384}$, Molecular Device, U.S.A.). The crystal structure of c-Met extracellular domain, accession number 1 SHY, was obtained from Protein Data Base (PDB). Computer imaging of the epitopes were analysed by PyMol (DeLano Scientific LLC, U.S.A.) software.

Western Blotting and Antibodies Used

The commercially-obtained SC-10 antibody (Santa Cruz, U.S.A.) was raised against a peptide within the C-terminal cytoplasmic region of human c-Met and would be expected to recognise c-Met precursor (170 kD) and mature c-Met β-chain (145 kD) on Western blots. AF276 antibody (R&D systems) is a goat antibody raised against the extracellular domain of c-Met. AF276 antibody would be expected to recognise c-Met precursor, mature c-Met β-chain and mature c-Met α-chain on Western blots. Both SC-10 and AF276 antibodies were used at 1:10 000 dilution on Western blotting. 1 µg/mL of anti-α-chain c-Met monoclonal antibody was used for Western blotting.

Protein samples were mixed with 4×LDS sample buffer (Invitrogen) and 10× sample reducing agent (Invitrogen) before analysing on 4-12% Bis-Tris gradient gels (Invitrogen) using MOPs buffer (Invitrogen). SeeBlue Plus2 protein ladder (Invitrogen) was used as molecular weight ladder. Transfer of proteins onto a nitrocellulose membrane (0.45 µm pore size, Whatman, United Kingdom) was performed using Bio-Rad wet transfer system for 2 hrs, at a constant current of 100 V. Transfer buffer contains 25 mM Tris, 192 mM and 20% methanol. Blocking buffer was made up of 5% Marvel milk in PBST (1% Tween 20 in PBS). Non-specific sites on the membrane were blocked in blocking buffer before incubating with primary antibodies. The membrane was washed three times and secondary antibodies were added at 1:10000 dilution in blocking buffer. Secondary antibodies conjugated to horseradish peroxidase (HRP) were obtained from Jacksons Laboratory/Stratech Scientific Ltd. (United Kingdom). Enhanced chemiluminescence (ECL) (Amersham/G.E. Healthcare, United Kingdom) was used for the detection of Western blots.

Immunoprecipitation

Cells lysates were obtained by lysing cells in NP40 lysis buffer as described above. 1 µg of purified antibody was incubated overnight with cell lysate (200 µg-500 µg of total protein in approximately 500 µL). Washed protein G beads (Sigma-Aldrich, U.S.A.) were added to the cell lysate. Beads were collected by centrifugation at 18,000×g and washed several times with NP40 lysis buffer. Bound proteins were eluted by adding 2×LDS sample buffer and the samples heated at 100° C. Beads were removed from eluate by centrifugating at 10,000×g. The eluate was analysed by SDS-PAGE gel.

Flow Cytometry

Flow cytometry was performed with help from Flow Cytometry Core Facility (College of Medicine, Dentistry and Nursing, University of Dundee, United Kingdom).

SNU-5 cells (1×10$^6$ cells) were washed once in cold PBS before blocking in 1% BSA/PBS. Cells were washed twice before incubating with anti-α-chain c-Met monoclonal antibodies. 1 µg/mL anti-α-chain monoclonal antibodies were used. Cells were incubated with goat anti-mouse IgG FITC-conjugated secondary antibodies (Invitrogen) and finally resuspended in 1% BSA/PBS. Flow cytometry was performed using Becton Dickinson (U.S.A.) FACScan. Cell Quest (Becton Dickinson) and FlowJo (Tree Star Inc., U.S.A.) software was used for data analysis.

Temperature Sensitivity

10 µg/mL of anti-α-chain monoclonal antibody were incubated with live SNU-5 cells for 1 hr at 4° C. or 37° C. Cells were harvested and washed once in cold PBS. Antibody binding to live cells was determined by Alexa Fluor®488-conjugated anti-mouse secondary antibodies (Invitrogen #A11029). Cells were resuspended in 1% BSA/PBS and analysed by flow cytometry.

Cell Scatter Assay 100-200 HaCaT cells were seeded in 24-well plates and allowed to grow until small colonies were formed (approximately 7 days). Cells were serum-starved for 24 hrs. Cells were incubated with purified monoclonal antibodies (1 µg/mL) for 24 hrs before rinsing twice in cold PBS and fixing in ice-cold methanol. Cells were then stained in 1% crystal-violet (Sigma-Aldrich) solution. Cell staining was observed using Zeiss Axiovert 25 inverted microscope and pictures were taken using a Canon EOS 1000 D camera.

Cell Viability and Caspase Activation

CellTiter-Glo® luminescent cell viability assay and Caspase-Glo® 3/7 Assay (Promega, U.S.A.) were used to determine cell viability and caspase activation respectively. SNU-5 cells (1×105 cells) were seeded in each 96-well and treated for 72 hrs before analysis. Cell viability and caspase activation were performed according to manufacturer's protocol. Luminescence was read using the EnVision plate reader (PerkinElmer, U.S.A.).

Cell Proliferation Using Cell Counter and CellTracker Green BODIPY Dye

Cell Count

Cells were seeded and treated with anti-α-chain c-Met monoclonal antibodies for 72 hrs. Cells were harvested and counted using the automated ADAM cell counter (Digital Bio, Korea).

CellTracker Green BODIPY Dye

SNU-5 cells were stained with 5 µM of CellTracker BODIPY dye for 30 mins. Stained cells were seeded and treated with anti-α-chain c-Met monoclonal antibodies for 6 days. Cells were harvested and dye retention in live cells were analysed by flow cytometry.

Immunofluorescence

10 µg/mL of anti-α-chain monoclonal antibody were incubated with live SNU-5 cells for 1 hr at 4° C. or 37° C. Antibody-treated cells were washed once with PBS and deposited onto polylysine-coated slides (Thermo Scientific, #5991056) using the Thermo Shandon Cytospin 3 Cytofuge (Thermo Scientific) at 800 rpm for 5 mins and fixed immediately in 4% paraformaldehyde. Cells were then blocked and permeablised in PBS containing 0.4% Triton X-100 and 5% BSA. Bound anti-α-chain c-Met antibodies were detected using anti-mouse Alexa Fluor®488-conjugated secondary antibody. Phallodin was added together with the secondary antibodies. Cells were washed before staining with 4',6'-diamidino-2-phenylindole (DAPI) and mounted with Hydromount (National Diagnostics, U.S.A.) containing 2.5% DABCO (1,4-Diazabicyclo-[2.2.2]octane) (Sigma-Aldrich) as an anti-bleaching agent Immunofluorescence was observed using Nikon Eclipse E600 microscope.

Comprehensive Mapping of mAb 2 Epitope

Figure 11:
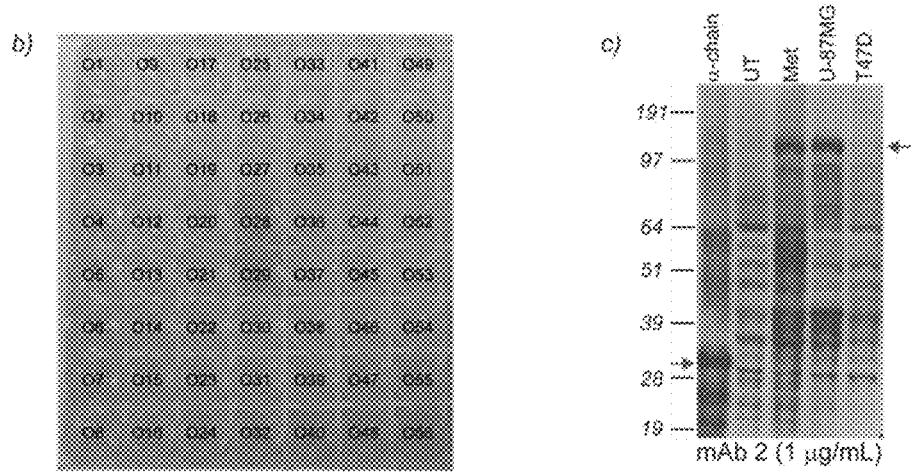
FIG. 11 shows under A) (SEQ ID NOs: 61-62 14-15 and B) a Pepscan, an ELISA-based assay, used to determine the region of mAb 2 epitope on c-Met α-chain. Consecutive overlapping peptides that span the entire human c-Met α-chain were synthesised and coated in 96-wells. To determine the binding region of mAb 2 on the α-chain, mAb 2 was added to each peptide. mAb 2 binding results in a colourmetric reaction which is analysed by absorbance reading at 450 nM. A) mAb 2 bound to peptides O28 and O29 with similar affinity. Sequence and binding affinity of peptides O1, O27, O28 and O29 are stated. B) Picture of mAb 2 pepscan analysis. mAb 2 binds to peptides O28 and O29 which results in a colorimetric reaction.
Figure 11:
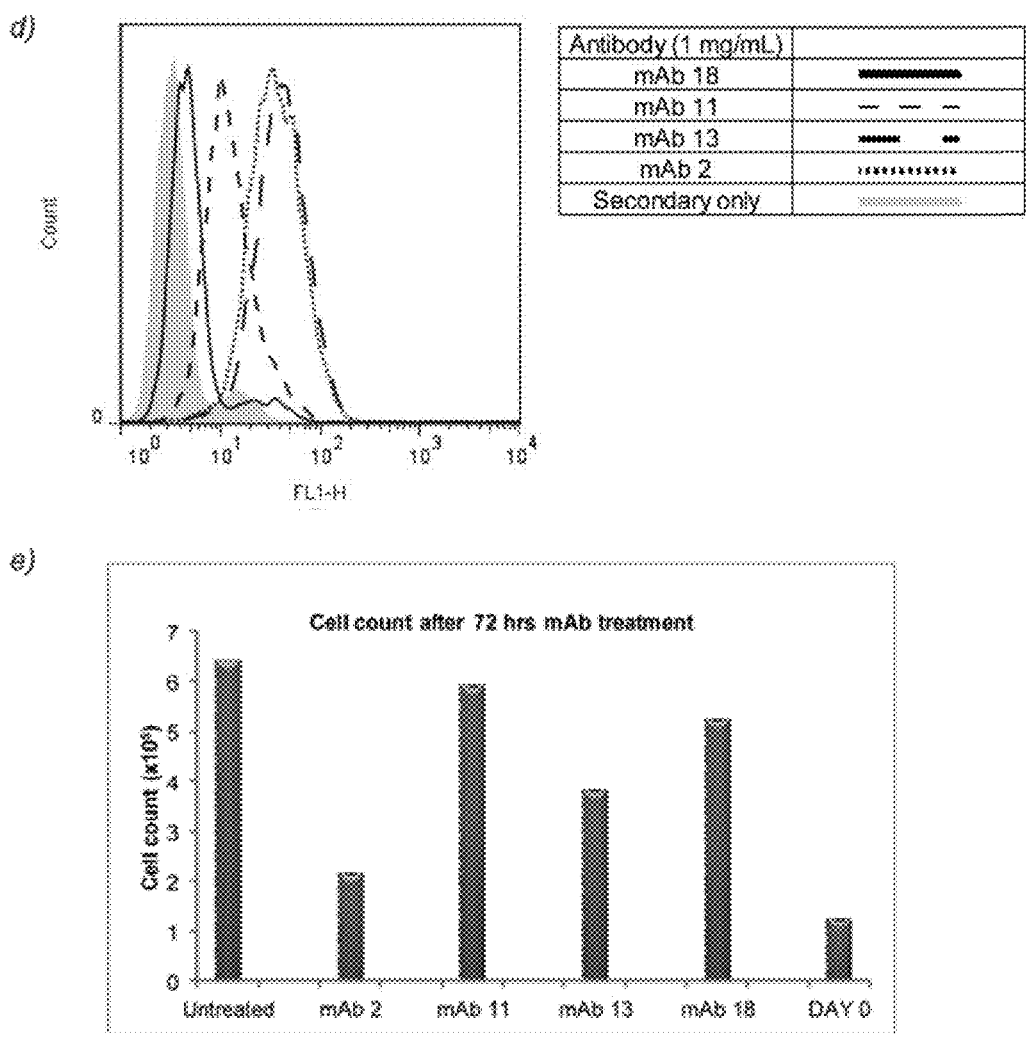

Pepscan analysis was used to determine the region of c-Met α-chain bound by mAb 2. Consecutive overlapping peptides that spanned the entire α-chain were synthesised in vitro (Mimotopes). Each peptide, made up of 15 amino acid residues, overlaps each neighbouring peptide by 10 amino acids. These peptides were tagged with biotin at the N-terminus through an SGSG linker sequence. Peptides were added to individual streptavidin-coated wells in a 96-well plate and unbound peptides were removed by extensive washing. To determine the region of mAb 2 binding on the α-chain, mAb 2 was added to each peptide containing well. Binding of the antibody was detected by colorimetric assay and analysed by absorbance reading at 450 nM.

mAb 2 bound to peptide O28 (CIFSPQIEEPSQCPD; SEQ ID NO: 14) and O29 (QIEEPSQCPDCVVSA; SEQ ID NO: 15) with similar affinity (FIG. 11A). This indicates that the epitope of mAb 2 is shared by both peptides. To identify residues within peptides O28 and O29 that are crucial for mAb 2-Met interaction, an alanine scan was performed. Variations of peptide O28 and O29, where each amino acid residue was sequentially substituted for an alanine residue, were synthesised (Table 3). Peptides P1 to P16 (with the SEQ II NO: 26 to 39) and P17 to P31. (with the SEQ ID NO: 40 to 56) were derived from the original peptide O28 and O29 respectively. Using the same ELISA-based assay described above, synthesised peptides were added to streptavidin-coated wells and purified mAb 2 was added to each peptide containing well. mAb 2 binding was determined by absorbance reading at 450 nM. Loss of antibody binding to a peptide demonstrates the importance of the substituted amino acid residue in mAb 2-Met interaction. Peptide O27, peptide O1 and no peptide were used as negative controls. Interestingly, although the first 10 amino acids of peptide O28 overlap with peptide O27, mAb 2 does not bind to peptide O27.

TABLE 3

Peptides used for mAb 2 alanine scan

| Original peptide | Peptide no. | Peptide sequence |
|---|---|---|
| O28 | P1 | AIFSPQIEEPSQCPD (SEQ ID NO: 26) |
| | P2 | CAFSPQIEEPSQCPD (SEQ ID NO: 27) |
| | P3 | CIASPQIEEPSQCPD (SEQ ID NO: 28) |
| | P4 | CIFAPQIEEPSQCPD (SEQ ID NO: 29) |
| | P5 | CIFSAQIEEPSQCPD (SEQ ID NO: 30) |
| | P6 | CIFSPAIEEPSQCPD (SEQ ID NO: 31) |
| | P7 | CIFSPQAEEPSQCPD (SEQ ID NO: 32) |
| | P8 | CIFSPQIAEPSQCPD (SEQ ID NO: 33) |
| | P9 | CIFSPQIEAPSQCPD (SEQ ID NO: 34) |
| | P10 | CIFSPQIEEASQCPD (SEQ ID NO: 35) |
| | P11 | CIFSPQIEEPAQCPD (SEQ ID NO: 40) |
| | P12 | CIFSPQIEEPSACPD (SEQ ID NO: 36) |
| | P13 | CIFSPQIEEPSQAPD (SEQ ID NO: 37) |
| | P14 | CIFSPQIEEPSQCAD (SEQ ID NO: 38) |
| | P15 | CIFSPQIEEPSQCPA (SEQ ID NO: 39) |
| | P16 | AIFSPQIEEPSQAPD (SEQ ID NO: 26) |
| O29 | P17 | AIEEPSQCPDCVVSA (SEQ ID NO: 41) |
| | P18 | QAEEPSQCPDCVVSA (SEQ ID NO: 42) |
| | P19 | QIAEPSQCPDCVVSA (SEQ ID NO: 43) |
| | P20 | QIEAPSQCPDCVVSA (SEQ ID NO: 44) |
| | P21 | QIEEASQCPDCVVSA (SEQ ID NO: 45) |
| | P22 | QIEEPAQCPDCVVSA (SEQ ID NO: 46) |
| | P23 | QIEEPSACPDCVVSA (SEQ ID NO: 46) |
| | P24 | QIEEPSQAPDCVVSA (SEQ ID NO: 48) |
| | P25 | QIEEPSQCADCVVSA (SEQ ID NO: 49) |
| | P26 | QIEEPSQCPACVVSA (SEQ ID NO: 50) |
| | P27 | QIEEPSQCPDAVVSA (SEQ ID NO: 51) |
| | P28 | QIEEPSQCPDCAVSA (SEQ ID NO: 52) |
| | P29 | QIEEPSQCPDCVASA (SEQ ID NO: 54) |
| | P30 | QIEEPSQCPDCVVAA (SEQ ID NO: 55) |
| | P31 | QIEEPSQAPDAVVSA (SEQ ID NO: 56) |

Figure 12:
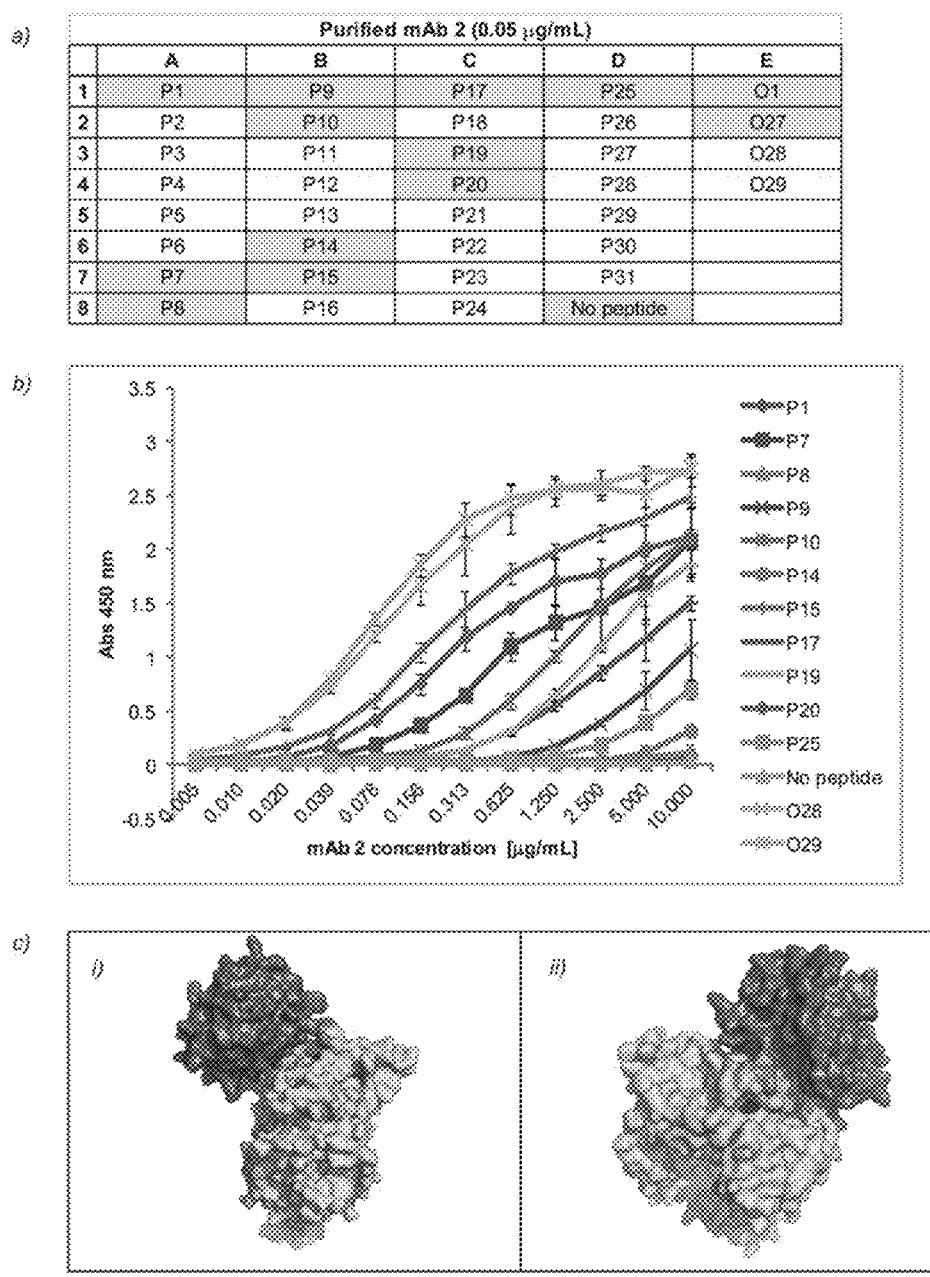
FIG. 12 are a table, a dot plot and a snapshot of a computer simulation representative of the experiments used for identification of the mAb 2 main epitope. A) Alanine scan analysis was used to determine the main residues involved in mAb 2 epitope. Peptides 1 to 31 are derivatives of peptides O28 and O29 where each amino acid residue is sequentially substituted for alanine. The peptide sequences are listed in Table 1. Using the same ELISA-based assay as pepscan, 0.05 µg/mL, of purified mAb 2 was added to the peptides in the presence of 1 mM DTT. mAb 2 binding was determined by absorbance reading at 450 nM. The lack of mAb 2 binding, highlighted in green, would indicate the involvement of the substituted residues in mAb 2-Met interaction. Peptides O1, O27 and no peptide were used as controls. B) Titration of purified mAb 2 against peptides. Alanine-substituted peptides that lost mAb 2 binding were titrated with increasing concentration of purified mAb 2. These peptides are listed in the order of increasing mAb 2 binding. C) Mapping of mAb 2 main epitope ('IEE' and 'CPDC') on c-Met crystal structure (PBD 1SHY). c-Met is highlighted in light grey, HGF in dark grey, 'IEE' residues (residue 166-168) in mid-grey and 'CPDC' residues (residues 172-175) in black. The protein complex is shown from two different viewpoints (i) and (ii) to allow visualisation of the mAb 2 main epitope in relation to ligand-receptor interaction site. Amino acid residue number is based on c-Met protein structure, PBD 1SHY.

In the presence of 1 mM DTT, the alanine scan analysis revealed that mAb 2 failed to bind to peptides P1, P7, P8, P9, P10, P14, P15, P17, P19, P20 and P25 (FIG. 12A). The substituted amino acid residues in these peptides are thus involved in mAb 2 epitope. Interestingly, prolines that form kinks in protein structures were observed to be important residues in mAb 2 epitope. This is supported by the loss of mAb 2 binding due to the substitution of proline by alanine in peptides P14, P25 and P10. To determine which residues play a more crucial role in mAb 2 binding, mAb 2 was titrated against the peptides (FIG. 12B). The peptides are listed in Table 4 in increasing binding affinity to mAb 2. mAb 2 bound peptides P1, P8 and P14 the least, indicating that the substituted residues, 'C', 'E' and 'P' respectively, are most critical for mAb 2 binding (FIG. 12B and Table 4). Further analysis of the peptides that fail to bind to mAb 2 showed that the residues 166 to 168 'IEE' and 172 to 175 'CPDC' form the main epitope of mAb 2. These residues are not consecutive residues. The importance of proline residues and the non-consecutive residues in mAb 2 main epitope suggests that the native structure of c-Met is important for mAb 2 binding. This is consistent with the observed character of mAb 2 i.e. mAb 2 have high affinity and specificity towards native c-Met and not to denatured c-Met (FIGS. 11C & D).

Mapping of mAb 2 main epitope, 'IEE' and 'CPDC', onto the crystal structure of c-Met (PBD 1SHY), revealed that 'IEE', in mid-grey, is exposed on the surface of c-Met while 'CPDC', in black, is buried within c-Met (FIG. 12C), How mAb 2 is able to bind to 'CPDC' is not yet known but it is speculated that this region could be more prominent in cancer cells. Computer simulation studies of mAb 2 binding will further elucidate this cryptic epitope of mAb 2.

TABLE 4

Alanine-substituted peptides listed in increasing order of mAb 2 binding.

| Increase mAb 2 binding in ascending order | Peptide no. | Peptide sequence |
|---|---|---|
| 1 | P1 | AIFSPQIEEPSQCPD (SEQ ID NO: 26) |
| | P8 | CIFSPQIAEPSQCPD (SEQ ID NO: 33) |
| 2 | P14 | CIFSPQIEEPSQCAD (SEQ ID NO: 38) |
| 3 | P25 | QIEEPSQCADCVVSA (SEQ ID NO: 49) |
| 4 | P9 | CIFSPQIEAPSQCPD (SEQ ID NO: 34) |
| 5 | P17 | AIEEPSQCPDCVVSA (SEQ ID NO: 41) |

TABLE 4-continued

Alanine-substituted peptides listed in increasing order of mAb 2 binding.

| Increase mAb 2 binding in ascending order | Peptide no. | Peptide sequence |
|---|---|---|
| 6 | P19 | QIAEPSQCPDCVVSA (SEQ ID NO: 43) |
| 7 | P10 | CIFSPQIEEASQCPD (SEQ ID NO: 35) |
| 8 | P7 | CIFSPQAEEPSQCPD (SEQ ID NO: 32) |
| 9 | P20 | QIEAPSQCPDCVVSA (SEQ ID NO: 44) |
| 10 | P15 | CIFSPQIEEPSQCPA (SEQ ID NO: 30) |
| 11 | O28 | CIFSPQIEEPSQCPD (SEQ ID NO: 14) |
|  | O29 | QIEEPSQCPDCVVSA (SEQ ID NO: 15) |

Phage Expression of mAb 2 scFv

Figure 15:
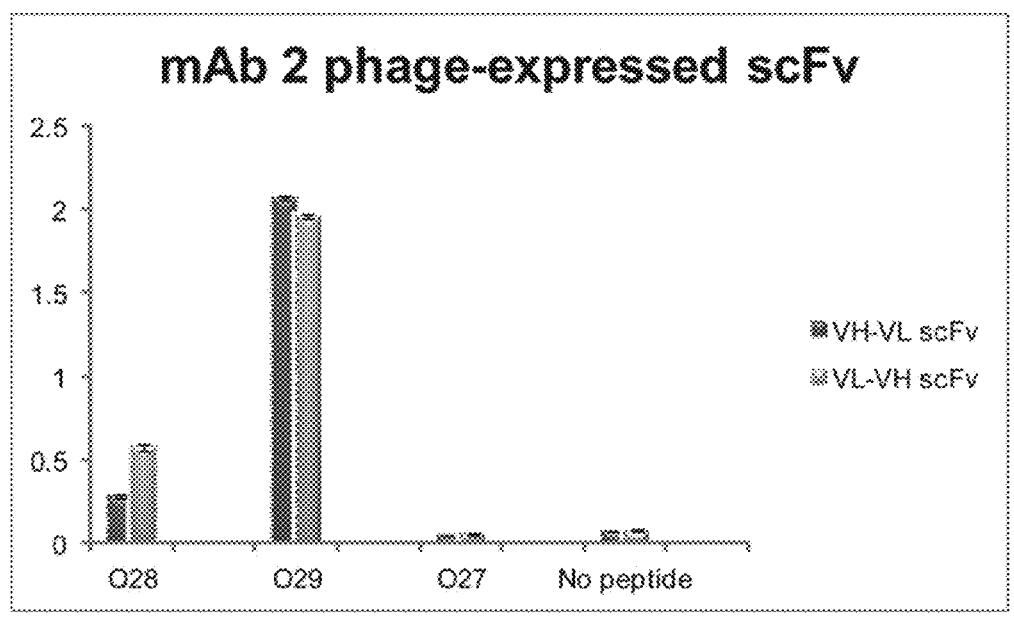
FIG. 15 is a bar graph showing the analysis of mAb 2 scFv binding by phage display. mAb 2 heavy and light chain were cloned and expressed on phage surface. mAb 2 scFv binding specificity towards peptides O28 (SEQ ID NO: 16) and O29 (SEQ ID NO: 17) were determined by ELISA. Peptide O27 and no peptides were used as controls. Two constructs of mAb 2 scFv were made: $V_H$ followed by $V_L$ ($V_H$-$V_L$) and $V_L$ followed by $V_H$ ($V_L$-$V_H$).

The variable regions of mAb 2 heavy (VH) and light (VL) chain were cloned into the phage expression vector pIT2 for antibody single-chain variable fragment (scFv) expression. Two mAb 2 scFv constructs were made: VH-VL scFv and VL-VH scFv. Nucleotide and protein sequences of mAb 2 heavy and light chain are listed in FIGS. 13 and 14 respectively.

mAb 2 scFv were expressed on phage surface. To determine if the phage-expressed scFv retained mAb 2 binding specificity, mAb 2 scFv-expressing phage were analysed for their binding to peptides O28 and O29. Using the same ELISA-based assay as described earlier, binding of mAb 2 scFv-expressing phage to peptides O28 and O29 were determined using HRP-conjugated anti-phage antibody. Absorbance was analysed at 450 nM. As negative controls, peptide O27 and no peptide control were used. Both mAb 2 scFv constructs bound to peptide O28 and O29 indicating that the VH and VL of mAb 2 were successfully cloned (FIG. 15). Interestingly, while full length murine mAb 2 showing no binding preference for peptides O28 and O29, both constructs of phage-expressed mAb 2 scFv bound more strongly to peptide O29 then to peptide O28. This could be due to the difference in antibody structure/framework. scFv is monovalent and lacked the antibody constant regions which also contains the flexible hinge region. This could affect the flexibility, binding avidity and binding affinity of an antibody.

The invention claimed is:

1. An antibody specifically binding an epitope comprised in the α-chain of c-Met, wherein the heavy chain of the antibody comprises:
   CDR 1 comprising the sequence of SEQ ID NO: 2;
   CDR 2 comprising the sequence of SEQ ID NO: 3;
   CDR 3 comprising the sequence of SEQ ID NO: 4; and
   wherein the light chain of the antibody comprises:
   CDR 1 comprising the sequence of SEQ ID NO: 5;
   CDR 2 comprising the sequence of SEQ ID NO: 6; and
   CDR 3 comprising the sequence of SEQ ID NO: 7.

2. The antibody of claim 1, wherein the antibody has a heavy chain comprising the sequence of SEQ ID NO:
   8 or a sequence which is at least 95%, or 96%, or 97%, or 98% identical to the sequence of SEQ ID NO: 8; and/or,
   wherein the antibody has a light chain comprising the sequence of SEQ ID NO: 9 or a sequence which is at least 95%, or 96%, or 97%, or 98% identical to the sequence of SEQ ID NO: 9.

3. The antibody of claim 2, wherein the antibody is coupled to an agent.

4. The antibody of claim 3, wherein the agent is a cytotoxic agent.

5. The antibody of claim 4, wherein the agent is selected from the group consisting of mertansine, emtansine, monomethyl auristatin E, ricin, diphtheria toxin, doxorubicin, *Pseudomonas aeruginosa* exotoxin, and pyrrolobenzodiazepine.

6. A nucleic acid encoding an antibody of claim 1, wherein the heavy chain of the antibody comprises the sequence as shown in SEQ ID NO: 10, and/or
   wherein the light chain of the antibody comprises the sequence as shown in SEQ ID NO: 11.

7. A pharmaceutical composition comprising an antibody of claim 1.

8. The pharmaceutical composition of claim 7 further comprising one or more pharmaceutically acceptable excipients, or vehicles, or carriers.

9. A method of treating and/or preventing cancer comprising administration of a therapeutically effective amount of an antibody of claim 1.

10. The method of claim 7, wherein cancer is selected from the group consisting of breast cancer, lung cancer, liver cancer, gastric cancer, brain cancer, blood cancer, colon cancer, pancreatic cancer and prostate cancer.

11. A method of diagnosing cancer comprising detection of aberrant expression of c-Met by administering an antibody of claim 1 for detecting c-Met.

* * * * *

SEQUENCE LISTING

```
<160> NUMBER OF SEQ ID NOS: 62

<210> SEQ ID NO 1
<211> LENGTH: 1390
<212> TYPE: PRT
<213> ORGANISM: Homo sapiens
<220> FEATURE:
<221> NAME/KEY: SIGNAL
<222> LOCATION: (1)..(25)
<223> OTHER INFORMATION: Signal peptide/Ig leader for secretion of Met
<220> FEATURE:
<221> NAME/KEY: CHAIN
<222> LOCATION: (26)..(307)
<223> OTHER INFORMATION: alpha chain
<220> FEATURE:
<221> NAME/KEY: CHAIN
<222> LOCATION: (308)..(1390)
<223> OTHER INFORMATION: beta chain

<400> SEQUENCE: 1

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125
```

-continued

```
Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Gly Gly Arg Phe Met Gln
450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
530                 535                 540
```

-continued

```
Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
            565                 570                 575

Gly Gly Thr Arg Leu Thr Ile Cys Gly Trp Asp Phe Gly Phe Arg Arg
        580                 585                 590

Asn Asn Lys Phe Asp Leu Lys Lys Thr Arg Val Leu Leu Gly Asn Glu
    595                 600                 605

Ser Cys Thr Leu Thr Leu Ser Glu Ser Thr Met Asn Thr Leu Lys Cys
610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
            645                 650                 655

Pro Val Ile Thr Ser Ile Ser Pro Lys Tyr Gly Pro Met Ala Gly Gly
        660                 665                 670

Thr Leu Leu Thr Leu Thr Gly Asn Tyr Leu Asn Ser Gly Asn Ser Arg
    675                 680                 685

His Ile Ser Ile Gly Gly Lys Thr Cys Thr Leu Lys Ser Val Ser Asn
690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
            725                 730                 735

Ser Tyr Arg Glu Asp Pro Ile Val Tyr Glu Ile His Pro Thr Lys Ser
        740                 745                 750

Phe Ile Ser Gly Gly Ser Thr Ile Thr Gly Val Gly Lys Asn Leu Asn
    755                 760                 765

Ser Val Ser Val Pro Arg Met Val Ile Asn Val His Glu Ala Gly Arg
770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
            805                 810                 815

Thr Lys Ala Phe Phe Met Leu Asp Gly Ile Leu Ser Lys Tyr Phe Asp
        820                 825                 830

Leu Ile Tyr Val His Asn Pro Val Phe Lys Pro Phe Glu Lys Pro Val
    835                 840                 845

Met Ile Ser Met Gly Asn Glu Asn Val Leu Glu Ile Lys Gly Asn Asp
850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
            885                 890                 895

Pro Asn Asp Leu Leu Lys Leu Asn Ser Glu Leu Asn Ile Glu Trp Lys
        900                 905                 910

Gln Ala Ile Ser Ser Thr Val Leu Gly Lys Val Ile Val Gln Pro Asp
    915                 920                 925

Gln Asn Phe Thr Gly Leu Ile Ala Gly Val Val Ser Ile Ser Thr Ala
        930                 935                 940

Leu Leu Leu Leu Leu Gly Phe Phe Leu Trp Leu Lys Lys Arg Lys Gln
945                 950                 955                 960

Ile Lys Asp Leu Gly Ser Glu Leu Val Arg Tyr Asp Ala Arg Val His
```

-continued

```
            965             970             975
Thr Pro His Leu Asp Arg Leu Val Ser Ala Arg Ser Val Ser Pro Thr
            980             985             990
Thr Glu Met Val Ser Asn Glu Ser Val Asp Tyr Arg Ala Thr Phe Pro
            995             1000            1005
Glu Asp Gln Phe Pro Asn Ser Ser Gln Asn Gly Ser Cys Arg Gln
    1010            1015            1020
Val Gln Tyr Pro Leu Thr Asp Met Ser Pro Ile Leu Thr Ser Gly
    1025            1030            1035
Asp Ser Asp Ile Ser Ser Pro Leu Leu Gln Asn Thr Val His Ile
    1040            1045            1050
Asp Leu Ser Ala Leu Asn Pro Glu Leu Val Gln Ala Val Gln His
    1055            1060            1065
Val Val Ile Gly Pro Ser Ser Leu Ile Val His Phe Asn Glu Val
    1070            1075            1080
Ile Gly Arg Gly His Phe Gly Cys Val Tyr His Gly Thr Leu Leu
    1085            1090            1095
Asp Asn Asp Gly Lys Lys Ile His Cys Ala Val Lys Ser Leu Asn
    1100            1105            1110
Arg Ile Thr Asp Ile Gly Glu Val Ser Gln Phe Leu Thr Glu Gly
    1115            1120            1125
Ile Ile Met Lys Asp Phe Ser His Pro Asn Val Leu Ser Leu Leu
    1130            1135            1140
Gly Ile Cys Leu Arg Ser Glu Gly Ser Pro Leu Val Val Leu Pro
    1145            1150            1155
Tyr Met Lys His Gly Asp Leu Arg Asn Phe Ile Arg Asn Glu Thr
    1160            1165            1170
His Asn Pro Thr Val Lys Asp Leu Ile Gly Phe Gly Leu Gln Val
    1175            1180            1185
Ala Lys Gly Met Lys Tyr Leu Ala Ser Lys Lys Phe Val His Arg
    1190            1195            1200
Asp Leu Ala Ala Arg Asn Cys Met Leu Asp Glu Lys Phe Thr Val
    1205            1210            1215
Lys Val Ala Asp Phe Gly Leu Ala Arg Asp Met Tyr Asp Lys Glu
    1220            1225            1230
Tyr Tyr Ser Val His Asn Lys Thr Gly Ala Lys Leu Pro Val Lys
    1235            1240            1245
Trp Met Ala Leu Glu Ser Leu Gln Thr Gln Lys Phe Thr Thr Lys
    1250            1255            1260
Ser Asp Val Trp Ser Phe Gly Val Val Leu Trp Glu Leu Met Thr
    1265            1270            1275
Arg Gly Ala Pro Pro Tyr Pro Asp Val Asn Thr Phe Asp Ile Thr
    1280            1285            1290
Val Tyr Leu Leu Gln Gly Arg Arg Leu Leu Gln Pro Glu Tyr Cys
    1295            1300            1305
Pro Asp Pro Leu Tyr Glu Val Met Leu Lys Cys Trp His Pro Lys
    1310            1315            1320
Ala Glu Met Arg Pro Ser Phe Ser Glu Leu Val Ser Arg Ile Ser
    1325            1330            1335
Ala Ile Phe Ser Thr Phe Ile Gly Glu His Tyr Val His Val Asn
    1340            1345            1350
Ala Thr Tyr Val Asn Val Lys Cys Val Ala Pro Tyr Pro Ser Leu
    1355            1360            1365
```

```
Leu Ser  Ser Glu Asp Asn Ala  Asp Asp Glu Val Asp  Thr Arg Pro
    1370             1375             1380

Ala Ser  Phe Trp Glu Thr Ser
    1385             1390
```

<210> SEQ ID NO 2
<211> LENGTH: 10
<212> TYPE: PRT
<213> ORGANISM: Homo sapiens

<400> SEQUENCE: 2

```
Gly Phe Thr Phe Thr Asp His Tyr Met Ser
1               5                   10
```

<210> SEQ ID NO 3
<211> LENGTH: 12
<212> TYPE: PRT
<213> ORGANISM: Homo sapiens

<400> SEQUENCE: 3

```
Phe Ile Arg Asn Lys Ala Lys Gly Tyr Thr Thr Glu
1               5                   10
```

<210> SEQ ID NO 4
<211> LENGTH: 9
<212> TYPE: PRT
<213> ORGANISM: Homo sapiens

<400> SEQUENCE: 4

```
Ala Arg Asp Gly Val Gly Ile Ala Tyr
1               5
```

<210> SEQ ID NO 5
<211> LENGTH: 16
<212> TYPE: PRT
<213> ORGANISM: Homo sapiens

<400> SEQUENCE: 5

```
Arg Ser Ser Gln Ser Leu Glu Asn Ile Asn Gly Asn Thr Tyr Leu Asn
1               5                   10                  15
```

<210> SEQ ID NO 6
<211> LENGTH: 7
<212> TYPE: PRT
<213> ORGANISM: Homo sapiens

<400> SEQUENCE: 6

```
Arg Val Ser Asn Arg Val Ser
1               5
```

<210> SEQ ID NO 7
<211> LENGTH: 9
<212> TYPE: PRT
<213> ORGANISM: Homo sapiens

<400> SEQUENCE: 7

```
Leu Gln Val Thr His Val Pro Trp Thr
1               5
```

<210> SEQ ID NO 8
<211> LENGTH: 123
<212> TYPE: PRT
<213> ORGANISM: Homo sapiens -continued

<400> SEQUENCE: 8

Ser Ile Val Met Thr Gln Ser Pro Leu Ser Leu Pro Val Ser Leu Gly
1               5                   10                  15

Asp Gln Ala Ser Ile Ser Cys Arg Ser Ser Gln Ser Leu Glu Asn Ile
            20                  25                  30

Asn Gly Asn Thr Tyr Lys Asn Trp Tyr Phe Gln Lys Pro Gly Gln Ser
        35                  40                  45

Pro Gln Leu Leu Ile Tyr Arg Val Ser Asn Arg Val Ser Gly Val Leu
    50                  55                  60

Asp Arg Phe Ser Gly Ser Gly Ser Gly Thr Asp Phe Thr Leu Lys Ile
65                  70                  75                  80

Thr Arg Val Glu Ala Glu Asp Leu Gly Val Tyr Phe Cys Leu Gln Val
                85                  90                  95

Thr His Val Pro Trp Thr Phe Gly Gly Gly Thr Lys Leu Glu Ile Lys
            100                 105                 110

Arg Ala Asp Ala Ala Pro Thr Lys Ser Ile Ser
            115                 120

<210> SEQ ID NO 9
<211> LENGTH: 130
<212> TYPE: PRT
<213> ORGANISM: Homo sapiens

<400> SEQUENCE: 9

Gln Val Gln Leu Lys Glu Ser Gly Gly Gly Leu Val Gln Pro Gly Gly
1               5                   10                  15

Ser Leu Thr Leu Ser Cys Ala Thr Ser Gly Phe Thr Phe Thr Asp His
            20                  25                  30

Tyr Met Ser Trp Val Arg Gln Pro Pro Gly Lys Ala Leu Glu Trp Leu
        35                  40                  45

Ala Phe Ile Arg Asn Lys Ala Lys Gly Tyr Thr Thr Glu Tyr Asn Ala
    50                  55                  60

Ser Val Arg Gly Arg Phe Thr Ile Ser Arg Asp Asn Ser Gln Asn Ile
65                  70                  75                  80

Val Tyr Leu Gln Met Asn Thr Leu Arg Thr Glu Asp Ser Ala Thr Tyr
                85                  90                  95

Tyr Cys Ala Arg Asp Gly Val Gly Ile Ala Tyr Trp Gly Gln Thr Leu
            100                 105                 110

Val Thr Val Ser Ala Ala Lys Thr Thr Pro Pro Ser Val Tyr Pro Leu
            115                 120                 125

Ala Pro
    130

<210> SEQ ID NO 10
<211> LENGTH: 15
<212> TYPE: PRT
<213> ORGANISM: Homo sapiens
<220> FEATURE:
<221> NAME/KEY: X1_6
<222> LOCATION: (1)..(6)
<223> OTHER INFORMATION: Any amino acid
<220> FEATURE:
<221> NAME/KEY: X10_12
<222> LOCATION: (10)..(12)
<223> OTHER INFORMATION: Any amino acid

<400> SEQUENCE: 10

Xaa Xaa Xaa Xaa Xaa Xaa Ile Glu Glu Xaa Xaa Xaa Cys Pro Asp
1               5                   10                  15

```
<210> SEQ ID NO 11
<211> LENGTH: 15
<212> TYPE: PRT
<213> ORGANISM: Homo sapiens
<220> FEATURE:
<221> NAME/KEY: X1
<222> LOCATION: (1)..(1)
<223> OTHER INFORMATION: Any amino acid
<220> FEATURE:
<221> NAME/KEY: X5_7
<222> LOCATION: (5)..(7)
<223> OTHER INFORMATION: Any amino acid
<220> FEATURE:
<221> NAME/KEY: X12_15
<222> LOCATION: (12)..(15)
<223> OTHER INFORMATION: Any amino acid

<400> SEQUENCE: 11

Xaa Ile Glu Glu Xaa Xaa Xaa Cys Pro Asp Cys Xaa Xaa Xaa Xaa
1               5                   10                  15

<210> SEQ ID NO 12
<211> LENGTH: 15
<212> TYPE: PRT
<213> ORGANISM: Homo sapiens
<220> FEATURE:
<221> NAME/KEY: X2_4
<222> LOCATION: (2)..(4)
<223> OTHER INFORMATION: Any amino acid
<220> FEATURE:
<221> NAME/KEY: X6
<222> LOCATION: (6)..(6)
<223> OTHER INFORMATION: Any amino acid
<220> FEATURE:
<221> NAME/KEY: X11_12
<222> LOCATION: (11)..(12)
<223> OTHER INFORMATION: Any amino acid

<400> SEQUENCE: 12

Cys Xaa Xaa Xaa Pro Xaa Ile Glu Glu Pro Xaa Xaa Cys Pro Asp
1               5                   10                  15

<210> SEQ ID NO 13
<211> LENGTH: 15
<212> TYPE: PRT
<213> ORGANISM: Homo sapiens
<220> FEATURE:
<221> NAME/KEY: X1
<222> LOCATION: (1)..(1)
<223> OTHER INFORMATION: Any amino acid
<220> FEATURE:
<221> NAME/KEY: X6_7
<222> LOCATION: (6)..(7)
<223> OTHER INFORMATION: Any amino acid
<220> FEATURE:
<221> NAME/KEY: X12_15
<222> LOCATION: (12)..(15)
<223> OTHER INFORMATION: Any amino acid

<400> SEQUENCE: 13

Xaa Ile Glu Glu Pro Xaa Xaa Cys Pro Asp Cys Xaa Xaa Xaa Xaa
1               5                   10                  15

<210> SEQ ID NO 14
<211> LENGTH: 15
<212> TYPE: PRT
<213> ORGANISM: Homo sapiens

<400> SEQUENCE: 14

Cys Ile Phe Ser Pro Gln Ile Glu Glu Pro Ser Gln Cys Pro Asp
```

<210> SEQ ID NO 15
<211> LENGTH: 15
<212> TYPE: PRT
<213> ORGANISM: Homo sapiens

<400> SEQUENCE: 15

Gln Ile Glu Glu Pro Ser Gln Cys Pro Asp Cys Val Val Ser Ala
1               5                   10                  15

<210> SEQ ID NO 16
<211> LENGTH: 369
<212> TYPE: DNA
<213> ORGANISM: Homo sapiens

<400> SEQUENCE: 16

```
agcattgtga tgacccagtc tccactctcc ctgcctgtca gtcttggaga tcaagcctcc      60
atctcttgca ggtctagtca gagccttgaa acattaatg  gaaacaccta tttgaactgg     120
tacttccaga aaccaggcca gtctccacag ctcctgatct acaggtttc  caaccgagtt     180
tctggggtcc tagacaggtt cagtggtagt ggatcaggga cagatttcac actgaaaatc     240
accagagtgg aggctgagga tttgggagtt tatttctgcc tccaagttac acatgtcccg     300
tggacgttcg gtggaggcac caaactggaa atcaaacggg ctgatgctgc accaactaag     360
tccatctcc                                                             369
```

<210> SEQ ID NO 17
<211> LENGTH: 394
<212> TYPE: DNA
<213> ORGANISM: Homo sapiens

<400> SEQUENCE: 17

```
caggtgcagc tgaaggagtc aggaggaggc ttggtacagc ctgggggtgt ctctgacact      60
ctcctgtgca acttctggat tcaccttcac tgatcactac atgagctggg tccgccagcc     120
tccaggaaag gcacttgagt ggttggcttt tatcagaaac aaagctaaag gttatacaac     180
agaatacaat gcatctgtga ggggtcggtt caccatctcc agagataatt cccaaaacat     240
cgtctatctt caaatgaaca ccctgagaac tgaggacagt gccacttatt actgtgcaag     300
agatggggtg ggaattgctt actggggcca agggactctg gtcactgttt ctgcagccaa     360
aacgacaccc ccatctgtct atccactggc ccct                                 394
```

<210> SEQ ID NO 18
<211> LENGTH: 30
<212> TYPE: DNA
<213> ORGANISM: Homo sapiens

<400> SEQUENCE: 18
ggattcacct tcactgatca ctacatgagc                                       30

<210> SEQ ID NO 19
<211> LENGTH: 36
<212> TYPE: DNA
<213> ORGANISM: Homo sapiens

<400> SEQUENCE: 19
tttatcagaa acaaagctaa aggttataca acagaa                                36

<210> SEQ ID NO 20

<211> LENGTH: 27
<212> TYPE: DNA
<213> ORGANISM: Homo sapiens

<400> SEQUENCE: 20
gcaagagatg gggtgggaat tgcttac                                        27

<210> SEQ ID NO 21
<211> LENGTH: 48
<212> TYPE: DNA
<213> ORGANISM: Homo sapiens

<400> SEQUENCE: 21
aggtctagtc agagccttga aaacattaat ggaaacacct atttgaac                 48

<210> SEQ ID NO 22
<211> LENGTH: 21
<212> TYPE: DNA
<213> ORGANISM: Homo sapiens

<400> SEQUENCE: 22
agggtttcca accgagtttc t                                              21

<210> SEQ ID NO 23
<211> LENGTH: 27
<212> TYPE: DNA
<213> ORGANISM: Homo sapiens

<400> SEQUENCE: 23
ctccaagtta cacatgtccc gtggacg                                        27

<210> SEQ ID NO 24
<211> LENGTH: 33
<212> TYPE: DNA
<213> ORGANISM: Homo sapiens

<400> SEQUENCE: 24
ggaattccat atggagtgta aagaggcact agc                                 33

<210> SEQ ID NO 25
<211> LENGTH: 35
<212> TYPE: DNA
<213> ORGANISM: Homo sapiens

<400> SEQUENCE: 25
gcggatccct atctcttttt tctcttttct gtgag                               35

<210> SEQ ID NO 26
<211> LENGTH: 15
<212> TYPE: PRT
<213> ORGANISM: Homo sapiens

<400> SEQUENCE: 26

Ala Ile Phe Ser Pro Gln Ile Glu Glu Pro Ser Gln Cys Pro Asp
1               5                   10                  15

<210> SEQ ID NO 27
<211> LENGTH: 15
<212> TYPE: PRT
<213> ORGANISM: Homo sapiens

<400> SEQUENCE: 27

Cys Ala Phe Ser Pro Gln Ile Glu Glu Pro Ser Gln Cys Pro Asp
1               5                   10                  15

```
<210> SEQ ID NO 28
<211> LENGTH: 15
<212> TYPE: PRT
<213> ORGANISM: Homo sapiens

<400> SEQUENCE: 28

Cys Ile Ala Ser Pro Gln Ile Glu Glu Pro Ser Gln Cys Pro Asp
1               5                   10                  15

<210> SEQ ID NO 29
<211> LENGTH: 15
<212> TYPE: PRT
<213> ORGANISM: Homo sapiens

<400> SEQUENCE: 29

Cys Ile Phe Ala Pro Gln Ile Glu Glu Pro Ser Gln Cys Pro Asp
1               5                   10                  15

<210> SEQ ID NO 30
<211> LENGTH: 15
<212> TYPE: PRT
<213> ORGANISM: Homo sapiens

<400> SEQUENCE: 30

Cys Ile Phe Ser Ala Gln Ile Glu Glu Pro Ser Gln Cys Pro Asp
1               5                   10                  15

<210> SEQ ID NO 31
<211> LENGTH: 15
<212> TYPE: PRT
<213> ORGANISM: Homo sapiens

<400> SEQUENCE: 31

Cys Ile Phe Ser Pro Ala Ile Glu Glu Pro Ser Gln Cys Pro Asp
1               5                   10                  15

<210> SEQ ID NO 32
<211> LENGTH: 15
<212> TYPE: PRT
<213> ORGANISM: Homo sapiens

<400> SEQUENCE: 32

Cys Ile Phe Ser Pro Gln Ala Glu Glu Pro Ser Gln Cys Pro Asp
1               5                   10                  15

<210> SEQ ID NO 33
<211> LENGTH: 15
<212> TYPE: PRT
<213> ORGANISM: Homo sapiens

<400> SEQUENCE: 33

Cys Ile Phe Ser Pro Gln Ile Ala Glu Pro Ser Gln Cys Pro Asp
1               5                   10                  15

<210> SEQ ID NO 34
<211> LENGTH: 15
<212> TYPE: PRT
<213> ORGANISM: Homo sapiens

<400> SEQUENCE: 34

Cys Ile Phe Ser Pro Gln Ile Glu Ala Pro Ser Gln Cys Pro Asp
1               5                   10                  15
```

<210> SEQ ID NO 35
<211> LENGTH: 15
<212> TYPE: PRT
<213> ORGANISM: Homo sapiens

<400> SEQUENCE: 35

Cys Ile Phe Ser Pro Gln Ile Glu Glu Ala Ser Gln Cys Pro Asp
1               5                   10                  15

<210> SEQ ID NO 36
<211> LENGTH: 15
<212> TYPE: PRT
<213> ORGANISM: Homo sapiens

<400> SEQUENCE: 36

Cys Ile Phe Ser Pro Gln Ile Glu Glu Pro Ser Ala Cys Pro Asp
1               5                   10                  15

<210> SEQ ID NO 37
<211> LENGTH: 15
<212> TYPE: PRT
<213> ORGANISM: Homo sapiens

<400> SEQUENCE: 37

Cys Ile Phe Ser Pro Gln Ile Glu Glu Pro Ser Gln Ala Pro Asp
1               5                   10                  15

<210> SEQ ID NO 38
<211> LENGTH: 15
<212> TYPE: PRT
<213> ORGANISM: Homo sapiens

<400> SEQUENCE: 38

Cys Ile Phe Ser Pro Gln Ile Glu Glu Pro Ser Gln Cys Ala Asp
1               5                   10                  15

<210> SEQ ID NO 39
<211> LENGTH: 15
<212> TYPE: PRT
<213> ORGANISM: Homo sapiens

<400> SEQUENCE: 39

Cys Ile Phe Ser Pro Gln Ile Glu Glu Pro Ser Gln Cys Pro Ala
1               5                   10                  15

<210> SEQ ID NO 40
<211> LENGTH: 15
<212> TYPE: PRT
<213> ORGANISM: Homo sapiens

<400> SEQUENCE: 40

Cys Ile Phe Ser Pro Gln Ile Glu Glu Pro Ala Gln Cys Pro Asp
1               5                   10                  15

<210> SEQ ID NO 41
<211> LENGTH: 15
<212> TYPE: PRT
<213> ORGANISM: Homo sapiens

<400> SEQUENCE: 41

Ala Ile Glu Glu Pro Ser Gln Cys Pro Asp Cys Val Val Ser Ala
1               5                   10                  15

<210> SEQ ID NO 42
<211> LENGTH: 15

```
<212> TYPE: PRT
<213> ORGANISM: Homo sapiens

<400> SEQUENCE: 42

Gln Ala Glu Glu Pro Ser Gln Cys Pro Asp Cys Val Val Ser Ala
1               5                   10                  15

<210> SEQ ID NO 43
<211> LENGTH: 15
<212> TYPE: PRT
<213> ORGANISM: Homo sapiens

<400> SEQUENCE: 43

Gln Ile Ala Glu Pro Ser Gln Cys Pro Asp Cys Val Val Ser Ala
1               5                   10                  15

<210> SEQ ID NO 44
<211> LENGTH: 15
<212> TYPE: PRT
<213> ORGANISM: Homo sapiens

<400> SEQUENCE: 44

Gln Ile Glu Ala Pro Ser Gln Cys Pro Asp Cys Val Val Ser Ala
1               5                   10                  15

<210> SEQ ID NO 45
<211> LENGTH: 15
<212> TYPE: PRT
<213> ORGANISM: Homo sapiens

<400> SEQUENCE: 45

Gln Ile Glu Glu Ala Ser Gln Cys Pro Asp Cys Val Val Ser Ala
1               5                   10                  15

<210> SEQ ID NO 46
<211> LENGTH: 15
<212> TYPE: PRT
<213> ORGANISM: Homo sapiens

<400> SEQUENCE: 46

Gln Ile Glu Glu Pro Ala Gln Cys Pro Asp Cys Val Val Ser Ala
1               5                   10                  15

<210> SEQ ID NO 47
<211> LENGTH: 15
<212> TYPE: PRT
<213> ORGANISM: Homo sapiens

<400> SEQUENCE: 47

Gln Ile Glu Glu Pro Ser Ala Cys Pro Asp Cys Val Val Ser Ala
1               5                   10                  15

<210> SEQ ID NO 48
<211> LENGTH: 15
<212> TYPE: PRT
<213> ORGANISM: Homo sapiens

<400> SEQUENCE: 48

Gln Ile Glu Glu Pro Ser Gln Ala Pro Asp Cys Val Val Ser Ala
1               5                   10                  15

<210> SEQ ID NO 49
<211> LENGTH: 15
<212> TYPE: PRT
```

<400> SEQUENCE: 49

Gln Ile Glu Glu Pro Ser Gln Cys Ala Asp Cys Val Val Ser Ala
1               5                   10                  15

<210> SEQ ID NO 50
<211> LENGTH: 15
<212> TYPE: PRT
<213> ORGANISM: Homo sapiens

<400> SEQUENCE: 50

Gln Ile Glu Glu Pro Ser Gln Cys Pro Ala Cys Val Val Ser Ala
1               5                   10                  15

<210> SEQ ID NO 51
<211> LENGTH: 15
<212> TYPE: PRT
<213> ORGANISM: Homo sapiens

<400> SEQUENCE: 51

Gln Ile Glu Glu Pro Ser Gln Cys Pro Asp Ala Val Val Ser Ala
1               5                   10                  15

<210> SEQ ID NO 52
<211> LENGTH: 15
<212> TYPE: PRT
<213> ORGANISM: Homo sapiens

<400> SEQUENCE: 52

Gln Ile Glu Glu Pro Ser Gln Cys Pro Asp Cys Ala Val Ser Ala
1               5                   10                  15

<210> SEQ ID NO 53
<211> LENGTH: 15
<212> TYPE: PRT
<213> ORGANISM: Homo sapiens

<400> SEQUENCE: 53

Gln Ile Glu Glu Pro Ser Gln Cys Pro Asp Cys Ala Val Ser Ala
1               5                   10                  15

<210> SEQ ID NO 54
<211> LENGTH: 15
<212> TYPE: PRT
<213> ORGANISM: Homo sapiens

<400> SEQUENCE: 54

Gln Ile Glu Glu Pro Ser Gln Cys Pro Asp Cys Val Ala Ser Ala
1               5                   10                  15

<210> SEQ ID NO 55
<211> LENGTH: 15
<212> TYPE: PRT
<213> ORGANISM: Homo sapiens

<400> SEQUENCE: 55

Gln Ile Glu Glu Pro Ser Gln Cys Pro Asp Cys Val Val Ala Ala
1               5                   10                  15

<210> SEQ ID NO 56
<211> LENGTH: 15
<212> TYPE: PRT
<213> ORGANISM: Homo sapiens

<400> SEQUENCE: 56

```
Gln Ile Glu Glu Pro Ser Gln Ala Pro Asp Ala Val Val Ser Ala
1               5                   10                  15
```

```
<210> SEQ ID NO 57
<211> LENGTH: 24
<212> TYPE: PRT
<213> ORGANISM: Homo sapiens

<400> SEQUENCE: 57
```

```
Met Lys Ala Pro Ala Val Leu Ala Pro Gly Ile Leu Val Leu Leu Phe
1               5                   10                  15

Thr Leu Val Gln Arg Ser Asn Gly
            20
```

```
<210> SEQ ID NO 58
<211> LENGTH: 284
<212> TYPE: PRT
<213> ORGANISM: Homo sapiens

<400> SEQUENCE: 58
```

```
Met Glu Cys Lys Glu Ala Leu Ala Lys Ser Glu Met Asn Val Asn Met
1               5                   10                  15

Lys Tyr Gln Leu Pro Asn Phe Thr Ala Glu Thr Pro Ile Gln Asn Val
            20                  25                  30

Ile Leu His Glu His His Ile Phe Leu Gly Ala Thr Asn Tyr Ile Tyr
        35                  40                  45

Val Leu Asn Glu Glu Asp Leu Gln Lys Val Ala Glu Tyr Lys Thr Gly
    50                  55                  60

Pro Val Leu Glu His Pro Asp Cys Phe Pro Cys Gln Asp Cys Ser Ser
65                  70                  75                  80

Lys Ala Asn Leu Ser Gly Gly Val Trp Lys Asp Asn Ile Asn Met Ala
                85                  90                  95

Leu Val Val Asp Thr Tyr Tyr Asp Asp Gln Leu Ile Ser Cys Gly Ser
            100                 105                 110

Val Asn Arg Gly Thr Cys Gln Arg His Val Phe Pro His Asn His Thr
        115                 120                 125

Ala Asp Ile Gln Ser Glu Val His Cys Ile Phe Ser Pro Gln Ile Glu
    130                 135                 140

Glu Pro Ser Gln Cys Pro Asp Cys Val Val Ser Ala Leu Gly Ala Lys
145                 150                 155                 160

Val Leu Ser Ser Val Lys Asp Arg Phe Ile Asn Phe Phe Val Gly Asn
                165                 170                 175

Thr Ile Asn Ser Ser Tyr Phe Pro Asp His Pro Leu His Ser Ile Ser
            180                 185                 190

Val Arg Arg Leu Lys Glu Thr Lys Asp Gly Phe Met Phe Leu Thr Asp
        195                 200                 205

Gln Ser Tyr Ile Asp Val Leu Pro Glu Phe Arg Asp Ser Tyr Pro Ile
    210                 215                 220

Lys Tyr Val His Ala Phe Glu Ser Asn Asn Phe Ile Tyr Phe Leu Thr
225                 230                 235                 240

Val Gln Arg Glu Thr Leu Asp Ala Gln Thr Phe His Thr Arg Ile Ile
                245                 250                 255

Arg Phe Cys Ser Ile Asn Ser Gly Leu His Ser Tyr Met Glu Met Pro
            260                 265                 270

Leu Glu Cys Ile Leu Thr Glu Lys Arg Lys Lys Arg
        275                 280
```

<210> SEQ ID NO 59
<211> LENGTH: 1083
<212> TYPE: PRT
<213> ORGANISM: Homo sapiens

<400> SEQUENCE: 59

```
Ser Thr Lys Lys Glu Val Phe Asn Ile Leu Gln Ala Ala Tyr Val Ser
1               5                   10                  15

Lys Pro Gly Ala Gln Leu Ala Arg Gln Ile Gly Ala Ser Leu Asn Asp
            20                  25                  30

Asp Ile Leu Phe Gly Val Phe Ala Gln Ser Lys Pro Asp Ser Ala Glu
        35                  40                  45

Pro Met Asp Arg Ser Ala Met Cys Ala Phe Pro Ile Lys Tyr Val Asn
    50                  55                  60

Asp Phe Phe Asn Lys Ile Val Asn Lys Asn Asn Val Arg Cys Leu Gln
65                  70                  75                  80

His Phe Tyr Gly Pro Asn His Glu His Cys Phe Asn Arg Thr Leu Leu
                85                  90                  95

Arg Asn Ser Ser Gly Cys Glu Ala Arg Arg Asp Glu Tyr Arg Thr Glu
            100                 105                 110

Phe Thr Thr Ala Leu Gln Arg Val Asp Leu Phe Met Gly Gln Phe Ser
        115                 120                 125

Glu Val Leu Leu Thr Ser Ile Ser Thr Phe Ile Lys Gly Asp Leu Thr
    130                 135                 140

Ile Ala Asn Leu Gly Thr Ser Glu Gly Arg Phe Met Gln Val Val Val
145                 150                 155                 160

Ser Arg Ser Gly Pro Ser Thr Pro His Val Asn Phe Leu Leu Asp Ser
                165                 170                 175

His Pro Val Ser Pro Glu Val Ile Val Glu His Thr Leu Asn Gln Asn
            180                 185                 190

Gly Tyr Thr Leu Val Ile Thr Gly Lys Lys Ile Thr Lys Ile Pro Leu
        195                 200                 205

Asn Gly Leu Gly Cys Arg His Phe Gln Ser Cys Ser Gln Cys Leu Ser
    210                 215                 220

Ala Pro Pro Phe Val Gln Cys Gly Trp Cys His Asp Lys Cys Val Arg
225                 230                 235                 240

Ser Glu Glu Cys Leu Ser Gly Thr Trp Thr Gln Gln Ile Cys Leu Pro
                245                 250                 255

Ala Ile Tyr Lys Val Phe Pro Asn Ser Ala Pro Leu Glu Gly Gly Thr
            260                 265                 270

Arg Leu Thr Ile Cys Gly Trp Asp Phe Gly Phe Arg Arg Asn Asn Lys
        275                 280                 285

Phe Asp Leu Lys Lys Thr Arg Val Leu Leu Gly Asn Glu Ser Cys Thr
    290                 295                 300

Leu Thr Leu Ser Glu Ser Thr Met Asn Thr Leu Lys Cys Thr Val Gly
305                 310                 315                 320

Pro Ala Met Asn Lys His Phe Asn Met Ser Ile Ile Ser Asn Gly
                325                 330                 335

His Gly Thr Thr Gln Tyr Ser Thr Phe Ser Tyr Val Asp Pro Val Ile
            340                 345                 350

Thr Ser Ile Ser Pro Lys Tyr Gly Pro Met Ala Gly Gly Thr Leu Leu
        355                 360                 365

Thr Leu Thr Gly Asn Tyr Leu Asn Ser Gly Asn Ser Arg His Ile Ser
```

```
            370                 375                 380
Ile Gly Gly Lys Thr Cys Thr Leu Lys Ser Val Ser Asn Ser Ile Leu
385                 390                 395                 400

Glu Cys Tyr Thr Pro Ala Gln Thr Ile Ser Thr Glu Phe Ala Val Lys
                405                 410                 415

Leu Lys Ile Asp Leu Ala Asn Arg Glu Thr Ser Ile Phe Ser Tyr Arg
                420                 425                 430

Glu Asp Pro Ile Val Tyr Glu Ile His Pro Thr Lys Ser Phe Ile Ser
                435                 440                 445

Gly Gly Ser Thr Ile Thr Gly Val Gly Lys Asn Leu Asn Ser Val Ser
                450                 455                 460

Val Pro Arg Met Val Ile Asn Val His Glu Ala Gly Arg Asn Phe Thr
465                 470                 475                 480

Val Ala Cys Gln His Arg Ser Asn Ser Glu Ile Ile Cys Cys Thr Thr
                485                 490                 495

Pro Ser Leu Gln Gln Leu Asn Leu Gln Leu Pro Leu Lys Thr Lys Ala
                500                 505                 510

Phe Phe Met Leu Asp Gly Ile Leu Ser Lys Tyr Phe Asp Leu Ile Tyr
                515                 520                 525

Val His Asn Pro Val Phe Lys Pro Phe Glu Lys Pro Val Met Ile Ser
                530                 535                 540

Met Gly Asn Glu Asn Val Leu Glu Ile Lys Gly Asn Asp Ile Asp Pro
545                 550                 555                 560

Glu Ala Val Lys Gly Glu Val Leu Lys Val Gly Asn Lys Ser Cys Glu
                565                 570                 575

Asn Ile His Leu His Ser Glu Ala Val Leu Cys Thr Val Pro Asn Asp
                580                 585                 590

Leu Leu Lys Leu Asn Ser Glu Leu Asn Ile Glu Trp Lys Gln Ala Ile
                595                 600                 605

Ser Ser Thr Val Leu Gly Lys Val Ile Val Gln Pro Asp Gln Asn Phe
                610                 615                 620

Thr Gly Leu Ile Ala Gly Val Val Ser Ile Ser Thr Ala Leu Leu Leu
625                 630                 635                 640

Leu Leu Gly Phe Phe Leu Trp Leu Lys Lys Arg Lys Gln Ile Lys Asp
                645                 650                 655

Leu Gly Ser Glu Leu Val Arg Tyr Asp Ala Arg Val His Thr Pro His
                660                 665                 670

Leu Asp Arg Leu Val Ser Ala Arg Ser Val Ser Pro Thr Thr Glu Met
                675                 680                 685

Val Ser Asn Glu Ser Val Asp Tyr Arg Ala Thr Phe Pro Glu Asp Gln
690                 695                 700

Phe Pro Asn Ser Ser Gln Asn Gly Ser Cys Arg Gln Val Gln Tyr Pro
705                 710                 715                 720

Leu Thr Asp Met Ser Pro Ile Leu Thr Ser Gly Asp Ser Asp Ile Ser
                725                 730                 735

Ser Pro Leu Leu Gln Asn Thr Val His Ile Asp Leu Ser Ala Leu Asn
                740                 745                 750

Pro Glu Leu Val Gln Ala Val Gln His Val Val Ile Gly Pro Ser Ser
                755                 760                 765

Leu Ile Val His Phe Asn Glu Val Ile Gly Arg Gly His Phe Gly Cys
                770                 775                 780

Val Tyr His Gly Thr Leu Leu Asp Asn Asp Gly Lys Lys Ile His Cys
785                 790                 795                 800
```

Ala Val Lys Ser Leu Asn Arg Ile Thr Asp Ile Gly Glu Val Ser Gln
                805                 810                 815

Phe Leu Thr Glu Gly Ile Ile Met Lys Asp Phe Ser His Pro Asn Val
            820                 825                 830

Leu Ser Leu Leu Gly Ile Cys Leu Arg Ser Glu Gly Ser Pro Leu Val
            835                 840                 845

Val Leu Pro Tyr Met Lys His Gly Asp Leu Arg Asn Phe Ile Arg Asn
        850                 855                 860

Glu Thr His Asn Pro Thr Val Lys Asp Leu Ile Gly Phe Gly Leu Gln
865                 870                 875                 880

Val Ala Lys Gly Met Lys Tyr Leu Ala Ser Lys Lys Phe Val His Arg
                885                 890                 895

Asp Leu Ala Ala Arg Asn Cys Met Leu Asp Glu Lys Phe Thr Val Lys
            900                 905                 910

Val Ala Asp Phe Gly Leu Ala Arg Asp Met Tyr Asp Lys Glu Tyr Tyr
        915                 920                 925

Ser Val His Asn Lys Thr Gly Ala Lys Leu Pro Val Lys Trp Met Ala
    930                 935                 940

Leu Glu Ser Leu Gln Thr Gln Lys Phe Thr Thr Lys Ser Asp Val Trp
945                 950                 955                 960

Ser Phe Gly Val Val Leu Trp Glu Leu Met Thr Arg Gly Ala Pro Pro
                965                 970                 975

Tyr Pro Asp Val Asn Thr Phe Asp Ile Thr Val Tyr Leu Leu Gln Gly
            980                 985                 990

Arg Arg Leu Leu Gln Pro Glu Tyr Cys Pro Asp Pro Leu Tyr Glu Val
        995                 1000                1005

Met Leu Lys Cys Trp His Pro Lys Ala Glu Met Arg Pro Ser Phe
    1010                1015                1020

Ser Glu Leu Val Ser Arg Ile Ser Ala Ile Phe Ser Thr Phe Ile
    1025                1030                1035

Gly Glu His Tyr Val His Val Asn Ala Thr Tyr Val Asn Val Lys
    1040                1045                1050

Cys Val Ala Pro Tyr Pro Ser Leu Leu Ser Ser Glu Asp Asn Ala
    1055                1060                1065

Asp Asp Glu Val Asp Thr Arg Pro Ala Ser Phe Trp Glu Thr Ser
    1070                1075                1080

<210> SEQ ID NO 60
<211> LENGTH: 4
<212> TYPE: PRT
<213> ORGANISM: Artificial Sequence
<220> FEATURE:
<223> OTHER INFORMATION: A synthetic CPDC sequence

<400> SEQUENCE: 60

Cys Pro Asp Cys
1

<210> SEQ ID NO 61
<211> LENGTH: 15
<212> TYPE: PRT
<213> ORGANISM: Homo sapiens

<400> SEQUENCE: 61

Glu Cys Lys Glu Ala Leu Ala Lys Ser Glu Met Asn Val Asn Met
1               5                   10                  15

```
<210> SEQ ID NO 62
<211> LENGTH: 15
<212> TYPE: PRT
<213> ORGANISM: Homo sapiens

<400> SEQUENCE: 62

Gln Ser Glu Val His Cys Ile Phe Ser Pro Gln Ile Glu Glu Pro
1               5                   10                  15
```